US008712791B2

(12) United States Patent
Dahlin et al.

(10) Patent No.: US 8,712,791 B2
(45) Date of Patent: Apr. 29, 2014

(54) SYSTEMS AND METHODS FOR DOCUMENTING MEDICAL FINDINGS OF A PHYSICAL EXAMINATION
(75) Inventors: Michael D. Dahlin, Austin, TX (US); Randolph B Lipscher, Austin, TX (US); Eric Wohl, Austin, TX (US)
(73) Assignee: Catalis, Inc., Austin, TX (US)
( * ) Notice: Subject to any disclaimer, the term of this patent is extended or adjusted under 35 U.S.C. 154(b) by 554 days.
(21) Appl. No.: 09/992,036
(22) Filed: Nov. 23, 2001
(65) Prior Publication Data
US 2004/0078215 A1 Apr. 22, 2004

Related U.S. Application Data
(60) Provisional application No. 60/252,872, filed on Nov. 22, 2000.
(51) Int. Cl.
G06Q 50/22 (2012.01)
G06Q 50/24 (2012.01)
(52) U.S. Cl.
USPC .................................................. 705/2; 705/3
(58) Field of Classification Search
USPC .......... 705/2, 3, 4, 8; 600/300, 437, 411, 104; 715/853, 807, 766, 788, 762, 234, 205; 707/104.1, 102; 345/173, 441
See application file for complete search history.

(56) References Cited

U.S. PATENT DOCUMENTS

| 4,839,822 A | 6/1989 | Dormond et al. |
| 4,858,121 A | 8/1989 | Barber et al. |

(Continued)

FOREIGN PATENT DOCUMENTS

| WO | WO 01/33378 A | 5/2001 |
| WO | WO 01/35376 A1 | 5/2001 |

(Continued)

OTHER PUBLICATIONS

Yoder, J. et al., The Medigate Graphical User Interface for Entry of Physical Findings: Design Principles and Implementation. Journal of Medical Systems. vol. 22, No. 5 / Oct. 1998, pp. 325-337. [Retrieved from Internet Apr. 12, 2008]. URL: <http://www.springerlink.com/content/g8504238744271h2/fulltext.pdf>.*

(Continued)

Primary Examiner — Lena Najarian
Assistant Examiner — Natalie A Pass
(74) Attorney, Agent, or Firm — Larson Newman, LLP

(57) ABSTRACT

An electronic system and a method for efficiently documenting medical findings that consist of both a problem and a location on or in the body. This invention further provides a method for documenting multiple problems in related body locations. This invention further provides a method for efficiently issuing orders associated with medical findings that consist of both a problem and a location on or in the body. The invention is able to enhance efficiency during the Physical exam making the invention an essential component of the physician's practice workflow. This, in turn, will enable the invention to serve as a single point of integration for a vast array of useful electronic tools and information. For example, in a computer-implemented system and method for documenting one or more medical findings having a body location and a type of medical finding, the method includes the steps of: displaying a body location selection view for a user, the user selecting a body location, the system then displaying a means of selecting possible types of medical findings, the system also then displaying a means of selecting to display a more detailed body location selection view, wherein the user selecting a type of medical finding causes the system to store a finding comprising the user-selected location and problem, and wherein the user selecting to display a more detailed body location selection view causes the system to display a more detailed body location selection view. The method may further include the finding types that may be selected are of a group of finding types and further comprising a means for selecting a different group of finding types to be displayed. Moreover, the groups of finding types each may correspond to a set of finding types related to one system of the body. The system may include a means for selecting one or more appropriate procedures that may be performed at the selected body location and a means for recording an annotation regarding the selected location of the body. The means for recording an annotation may be selected from a group including selecting a pre-generated annotation, recording a text annotation, recording a graphical annotation, recording a sound annotation, and recording a photographic annotation.

23 Claims, 27 Drawing Sheets

(56) References Cited

U.S. PATENT DOCUMENTS

| | | | |
|---|---|---|---|
| 4,916,611 A | 4/1990 | Doyle, Jr. et al. | |
| 5,018,067 A | 5/1991 | Mohlenbrock et al. | |
| 5,065,315 A | 11/1991 | Garcia | |
| 5,070,452 A | 12/1991 | Doyle, Jr. et al. | |
| 5,072,383 A | 12/1991 | Brimm et al. | |
| 5,077,666 A | 12/1991 | Brimm et al. | |
| 5,101,476 A | 3/1992 | Kukla | |
| 5,301,105 A | 4/1994 | Cummings, Jr. | |
| 5,319,543 A | 6/1994 | Wilhelm | |
| 5,347,453 A | 9/1994 | Maestre | |
| 5,347,477 A | 9/1994 | Lee | |
| 5,361,202 A | 11/1994 | Doue | |
| 5,366,896 A | 11/1994 | Margrey et al. | |
| 5,390,238 A | 2/1995 | Kirk et al. | |
| 5,528,021 A | 6/1996 | Lassus et al. | |
| 5,561,446 A | 10/1996 | Montlick | |
| 5,594,638 A | 1/1997 | Iliff | |
| 5,660,176 A | 8/1997 | Iliff | |
| 5,722,418 A | 3/1998 | Bro | |
| 5,737,539 A | 4/1998 | Edelson et al. | |
| 5,748,907 A | 5/1998 | Crane | |
| 5,769,074 A | 6/1998 | Barnhill et al. | |
| 5,772,585 A | 6/1998 | Lavin et al. | |
| 5,778,882 A | 7/1998 | Raymond et al. | |
| 5,845,255 A | 12/1998 | Mayaud | |
| 5,868,669 A | 2/1999 | Iliff | |
| 5,879,163 A | 3/1999 | Brown et al. | |
| 5,883,370 A | 3/1999 | Walker et al. | |
| 5,924,074 A | 7/1999 | Evans | |
| 5,946,646 A | 8/1999 | Schena et al. | |
| 5,951,300 A | 9/1999 | Brown | |
| 5,954,641 A | 9/1999 | Kehr et al. | |
| 5,960,085 A | 9/1999 | de la Huerga | |
| 5,992,890 A | 11/1999 | Simcox | |
| 6,018,713 A | 1/2000 | Coli et al. | |
| 6,021,202 A | 2/2000 | Anderson et al. | |
| 6,024,699 A | 2/2000 | Surwit et al. | |
| 6,026,363 A | 2/2000 | Shepard | |
| 6,047,259 A * | 4/2000 | Campbell et al. | 705/3 |
| 6,055,333 A | 4/2000 | Guzik et al. | |
| 6,073,097 A | 6/2000 | Gould et al. | |
| 6,073,375 A | 6/2000 | Fant et al. | |
| 6,085,752 A | 7/2000 | Kehr et al. | |
| 6,090,044 A | 7/2000 | Bishop et al. | |
| 6,108,635 A | 8/2000 | Herren et al. | |
| 6,113,540 A | 9/2000 | Iliff | |
| 6,132,218 A | 10/2000 | Benja-Athon | |
| 6,161,095 A | 12/2000 | Brown | |
| 6,206,829 B1 | 3/2001 | Iliff | |
| 6,209,095 B1 | 3/2001 | Anderson et al. | |
| 6,215,901 B1 * | 4/2001 | Schwartz | 382/186 |
| 6,248,063 B1 | 6/2001 | Barnhill et al. | |
| 6,298,348 B1 | 10/2001 | Eldering | |
| 6,317,789 B1 | 11/2001 | Rakavy et al. | |
| 6,347,329 B1 | 2/2002 | Evans | |
| 6,383,135 B1 * | 5/2002 | Chikovani et al. | 600/300 |
| 6,385,592 B1 | 5/2002 | Angles et al. | |
| 6,454,708 B1 | 9/2002 | Ferguson et al. | |
| 6,609,200 B2 | 8/2003 | Anderson et al. | |
| 6,678,669 B2 | 1/2004 | Lapointe et al. | |
| 6,839,678 B1 | 1/2005 | Schmidt et al. | |
| 2001/0023419 A1 | 9/2001 | Lapointe et al. | |
| 2001/0032099 A1 | 10/2001 | Joao | |
| 2001/0032124 A1 | 10/2001 | Savage et al. | |
| 2001/0041992 A1 * | 11/2001 | Lewis et al. | 705/3 |
| 2002/0049612 A1 | 4/2002 | Jaeger et al. | |
| 2003/0018495 A1 | 1/2003 | Sussman | |

FOREIGN PATENT DOCUMENTS

| | | |
|---|---|---|
| WO | WO 02/33654 A1 | 4/2002 |
| WO | WO 02/42875 A2 | 5/2002 |
| WO | WO 02/42876 A2 | 5/2002 |
| WO | WO 2004/015543 A2 | 2/2004 |
| WO | WO 2004/051415 A2 | 6/2004 |
| WO | WO 2004/051428 A2 | 6/2004 |
| WO | WO 2004/051628 A2 | 6/2004 |

OTHER PUBLICATIONS

Yoder, J. The Role of Human-Computer Interaction in Medical Information Systems: Principles and Implementation of Medigate. MS Thesis, University of Illinois at Urbana-Champaign, Department of Computer Science, 1992. [Retrieved from Internet Sep. 13, 2009]. URL: <http://citeseerx.ist.psu.edu/viewdoc/download?doi=10.1.1.66.8039&rep=rep1&type=pdf>.*

Sanger, J. Graphic User Interface-Based Nuclear Medicine Reporting System. J Nucl Med 34: 515-522. 1992. [Retrieved from Internet Sep. 13, 2009]. URL: <http://jnm.snmjournals.org/cgi/reprint/34/3/515.pdf >.*

Gorzalczany, M. B.; Gradzki, P., Computational intelligence in medical decision support a comparison of two neuro-fuzzy systems, Industrial Electronics, 1999, ISIE '99. Proceedings of the IEEE International Symposium on, vol. 1, 1999, pp. 408-413, vol. 1.

Tzanidou, Ekaterini (2006). "Eye tracking as a complementary usability evaluation technique for e-commerce sites," Extract from PhD Thesis, The Open University.

Kostaras et al., "A study on how usability flaws in GUI design increase mouse movement and consequently may affect user health," Journal of Behaviour and Information Technology, vol. 30, issue 3, May 2011.

* cited by examiner

SYSTEMS AND METHODS FOR DOCUMENTING MEDICAL FINDINGS OF A PHYSICAL EXAMINATION

RELATED APPLICATIONS

This application claims priority of U.S. patent Application, Ser. No. 60/252,872, filed Nov. 22, 2000, entitled: "SYSTEM AND METHODS FOR DOCUMENTING MEDICAL FINDINGS OF A PHYSICAL EXAMINATION", and is incorporated herein by reference.

TECHNICAL FIELD OF THE INVENTION

The present invention relates to the field of health care delivery and, in particular, to an electronic system that facilitates documenting medical findings of a physical examination in a medical practitioner-patient encounter and that can serve as a single point of integration for electronic health care information systems.

BACKGROUND OF THE INVENTION

To improve efficiency of medical practitioners and to curtail the rising cost of providing health care, many attempts have been made to use computers or electronic medical records (EMR) systems to facilitate the delivery of a variety of health care services. Such systems have generally been poorly integrated with the medical practitioner's workflow and have not been widely adopted.

Medical practitioners generally spend most of their medical practice workday servicing patients. Over time, most medical practitioners have derived a process of the medical practitioner-patient encounter ("the Physical Exam") that divides it into two main discrete parts, with each part either produces or employs specific health-related information. Such health-related information generally falls into two information segments: anatomical and diagnostic. Typically, anatomical and diagnostic information includes: historical health information, including symptoms described by the patient; physical examination observations, including objective findings by the medical practitioner; assessment, including diagnosis, differential diagnosis, working diagnosis; and plan, which may include: diagnostic or treatment procedure; scheduling of procedures, referral and/or reassessment; information/education for patient; projected care plan and other processes and functions appropriate to each given diagnosis for a particular patient.

For a diagnosis, in the process and flow of the Physical exam, both anatomical and diagnostic information may be utilized to generate and record one or more medical findings. Such medical findings are generally documented for later review, but are also created as a result of the Physical exam and are used to initiate one or more procedures that result from the physical exam.

The health-related information processed in the Physical exam either generates or employs descriptive health-related data which can be classified into two groups: "anatomical data," such as historical data and physical examination findings, and "diagnostic data," such as diagnoses and care plans. Applicants have discovered that a primary reason prior efforts to automate the Physical exam have met with limited success is because of a failure to coordinate processing of anatomical data and diagnostic data. Descriptive health-related data can comprise an unlimited number of combinations of terms and is, therefore, inherently intractable. To handle descriptive health-related data, each individual medical practitioner develops his or her own preferred terminology and approach to recording the data, ranging from transcription to handwriting, to hiring staff to write or record for them. Automating such unruly data has not been efficient. Moreover, because of the wide variety of methods adopted by individual medical practitioners for handling such data, efforts to automate the collection of descriptive health-related data typically disrupt the established work flow patterns of the medical practitioners.

In a majority of EMR systems, efforts to integrate computer technology into the medical practitioner-patient encounter have largely focused on digitally recording the medical findings—learned during the Physical exam for later review, analysis or for electronic transmission and reproduction. These electronic medical records systems fail to facilitate the medical practitioner conducting the physical exam itself. Existing EMRs are highly structured to accommodate the complexity of medical practice, whereas medical practitioners' medical practices are typically highly individualized. The resulting conflict between personal work style and a structured electronic medical record system generally disrupts the physical exam, rather than facilitate it as intended. Because of these limitations, such systems have not gained wide acceptance in the medical community.

Some attempts have been made to computerize specific aspects of health care delivery apart from the clinical patient record. These limited attempts, or "point solutions," include for example, expert systems that purportedly assist a medical practitioner in reaching a diagnosis or in selecting a proper drug dosage. Such systems are not popular with medical practitioners because, like the EMR systems, they disrupt the medical practitioners' workflow, thereby decreasing productivity. Moreover, medical practitioners typically do not require the assistance of an expert system to reach a diagnosis.

While offering enhanced capabilities, related medical electronic art, has proven to be less efficient than pen and paper. The medical practitioner's need for efficiency outweighs the need for improved functionality. Thus, the need for a system to electronically facilitate the medical practitioner's workday remains largely unfulfilled, and medical practitioners rely primarily on handwritten documentation.

In order to improve the efficiency of medical practitioners, several electronic medical records (EMR) systems have been created. These EMR systems allow medical practitioners to review records, document findings, and issue orders.

However, in the past, EMR systems were primarily used for data storage, record recall, and other operations at a time or place separate from the actual medical practitioner-patient encounter. The emergence of portable computer technology—including laptop computer devices, tablet form-factor devices such as the National Semiconductor WebPad demonstration system, and handheld form-factor devices such as the Palm, Inc. Palm V computer—allows medical practitioners to utilize EMR systems while working with patients. However, this mode of operation places a further premium on efficiency, since the user must quickly enter data as the patient describes problems or as the practitioner examines the patient. Thus, in constructing an EMR system for these new technologies, efficiency is paramount. A medical practitioner must be able to quickly select a data element to add to a medical record.

Some medical findings can only occur in one or a small number of locations on or in the body. An example is the finding "cardiovascular S3 present", which identifies both the structure of the body that is affected and the problem with that structure. These medical findings are relatively easy to document efficiently with currently known methods. For example, a system may implement a process in which the user first selects the system of the body ("cardiovascular") and then selects the finding ("S3 present").

A number of EMR systems to document this type of finding exist. In such systems, a user typically selects a system and is presented with a list of findings for that system. For example, the Medcin system provides an interface of this type. This simple approach is feasible for this type of medical finding because the number of common medical findings per system is typically small enough to allow the list to fit on a single display and because once the medical finding is selected, there is no need to further specify the location of the body.

Unfortunately, it is difficult to document significantly more complex types of medical findings—medical findings for which both a medical problem and a body location must be documented and especially, in the case that location must be chosen from a wide range of possibilities. Examples may include many muskulo-skeletal system findings (e.g., sprains, fracture, or dislocation) or skin system medical findings (e.g., abrasion, laceration, or burn). The challenge to documenting such medical findings efficiently is that navigation through the space of options proceeds in two dimensions. Moreover, it could be even more difficult to provide a system that enables freedom to navigate, that makes it efficient to document a series of related medical problems in related locations of the body while making the whole documenting process relatively efficient.

Some EMR systems require a user to first specify a problem and then specify the location. A problem with these systems is that they make it difficult for a user to document multiple problems in the same location. On the other hand, some EMR systems attempt to document such findings by requiring a user to first specify a location and then specify the problem. However, for the types of medical findings under consideration, the number of locations may be too large and body location selection could be typically a multi-step process. For example, first a general region of the body is selected (e.g., left arm), then a more detailed location is selected (e.g., left wrist), finally a specific location is selected (e.g., left scaphoid bone). The difficulty is that the level of detail that a finding location is to be specified depends on the finding medical problem as well as other circumstances such as the user's preferences or judgement (e.g., one doctor may wish to indicate "cut on right hand" while another might document "cut from base of second finger to wrist of right hand" for the same injury), severity of the problem (a doctor might document the location of a deep cut more precisely than that of a shallow cut), clinic specialty (e.g., in a major trauma case, an emergency room doctor might document "left wrist fracture" and not provide additional details since the doctor's attention might be focused on more serious problems; later, an orthopedist treating the same patient might document "left scaphoid fracture").

Consequently, at a given step of navigation, choosing a location might be intended to (a) drill down to provide options to select more detailed locations or (b) select the location as the terminal location of the problem. One approach to using a location-then-problem navigation method might require the user to first "drill down" to a picture that shows the location of the problem in the desired level of detail, to then explicitly exit "drill down" navigation mode to enter selection mode, to then select the location of the problem, and to finally select the problem. Note that if the user forgets to exit "drill down" mode, when the user selects a location, the system will drill down to a more detailed view, rather than selecting the location as the user intended. This extra step is thus both confusing and inefficient.

In a typical medical practice, it is common to add free text notation to findings using, for example, handwritten notes on a clipboard, dictated notes that are recorded and transcribed. However, current electronic medical records systems make such annotation difficult to perform efficiently because (a) this notation is not integrated into an efficient system for entering findings and (b) the means for entering these notations is cumbersome, involving free-end character-recognition text or recorded voice that is transcribed to text off line. What is needed is a system that integrates such nuanced descriptions into an electronic medical record for efficiently documenting findings or collections of findings at a location and that makes documenting complex annotations efficient by combining free-form input of text and graphics with (more efficient but less flexible) list selection input.

Moreover, it is desirable to document medical findings that require more detail than simply a problem, location, and state. In addition there is a need for a system and method to efficiently document multiple medical problems that are located near one another in the body. For example, an emergency room doctor treating a hand damaged in an industrial accident might need to document cuts to several fingers and the hand as well as broken bones in the several fingers and the hand. Such situations create a requirement for a method and system that efficiently coordinates navigation to different related body locations, selection of related body locations, and selection of multiple medical problems.

SUMMARY OF THE INVENTION

A system for documenting one or more medical findings of a physical examination, the system includes an interactive device having an output interface and an input interface, the output interface for displaying to a user, health-related information including anatomical information having a list of body systems (optionally) and a plurality of body locations and diagnostic information having a plurality of medical problems, and the input interface for the user to navigate the displayed anatomical information and diagnostic information for deriving the one or more medical findings, each medical finding comprising at least one selected medical problem corresponding to at least one selected body location; a memory for storing a computer program; a processor for executing the computer program, the computer program processing the one or more medical findings; and a data storage device for storing the one or more medical findings.

One embodiment of the invention is based on a method for documenting medical findings of a physical examination, the method including: displaying anatomical information including a list of body systems (optionally) and a plurality of body locations, in a first view; accepting from a user a first selection from the anatomical information including at least one body system (optionally) and one or more body locations related to the physical examination; displaying diagnostic information including a plurality of medical problems, in a second view, responsive to the first selection; accepting from the user a second selection from the diagnostic information including one or more medical problems; and combining the first and second selections to derive at least one medical finding.

Another embodiment of the invention provides a system for documenting one or more medical findings of a physical examination, the system comprising: an interactive device having an output interface and an input interface, the output interface for displaying to a user, health-related information including anatomical information and diagnostic information, and the input interface for the user to navigate the displayed anatomical information and diagnostic information for deriving the one or more medical findings, each medical finding comprising at least an associated medical problem corresponding to a body location; a data storage device for storing the one or more medical findings; a memory for storing a computer program; and a processor for executing the computer program, the computer program processing the one or more medical findings, by: displaying in a first view through the output interface the anatomical information including a list of body systems (optionally) and a plurality of body locations; accepting from the user a first selection from the anatomical information including at least one body system (optionally) and one or more body locations related to the physical examination, the selected anatomical information being entered through the input interface in the first view; automatically displaying in a second view the diagnostic information including a plurality of medical problems consistent with the anatomical information, the plurality of medical problems being displayed through the output interface in a specific order selected by the user; accepting from the user a second selection from the diagnostic information including one or more medical problems, the selected diagnostic information being entered through the input interface in the second view; and combining the selected one or more body locations with the selected one or more medical problems corresponding to the one or more medical findings for the selected at least one body system (optionally).

Another alternate embodiment of the invention is based on a computer-implemented method for documenting medical findings of a physical examination, the method including: presenting to a user a list of body systems; selecting from the list of body systems at least one body system related to the physical examination; presenting to the user a first display having a plurality of body locations; selecting from the plurality of body locations at least one body location related to the physical examination; presenting to the user a second display having a plurality of medical problems; selecting from the plurality of medical problems at least one medical problem corresponding to the selected body system and the selected body location; and storing the combination of the selected body location and the selected medical problem as a medical finding for the selected body system.

Another alternate embodiment of the invention is based on a computer-implemented method for documenting medical findings of a physical examination, the method including: presenting to the user a list of body systems including a first body system related to the physical examination; selecting from the list of body systems the first body system; presenting to the user a first display of a plurality of body locations including a first body location and a second body location, wherein the first and second body locations related to the physical examination; selecting from the plurality of body locations one or more body locations including the first body location and the second body location; presenting to the user a second display having a plurality of medical problems including a first medical problem and a second medical problem; selecting from the plurality of medical problems one or more medical problems including the first medical problem corresponding to the first body location, and the second medical problem corresponding to the second body location, wherein the first and second medical problems related to the first body system; and storing a first combination of the first body location with the first medical problem, and a second combination of the second body location with the second medical problem, wherein the first and second combinations indicate a medical finding for the first body system.

Another alternate embodiment of the invention is based on a computer-implemented method for documenting medical findings of a physical examination, the method including: presenting to a user a list of body systems including a first body system, the first body system determined to be associated with the physical examination; selecting from the list of body systems the first body system; presenting to the user a first display of a plurality of body locations including a first body location, the first body location determined to be associated with the physical examination; selecting from the plurality of body locations the first body location; presenting to the user a second display having a plurality of medical problems including a first medical problem and a second medical problem, wherein the first and second medical problems determined to be associated with the physical examination; selecting from the plurality of medical problems the first and second medical problems; and storing a combination of the first body location with the first and second medical problems as a medical finding for the first body system.

Another alternate embodiment of the invention is based on a computer-implemented method for documenting medical findings of a physical examination, the method including: presenting to a user a list of body systems including a first body system, the first body system determined to be associated with the physical examination; selecting from the list of body systems the first body system; presenting to the user a first display of a plurality of body locations including a first body location and a second body location, the first and second body locations determined to be associated with the physical examination; selecting from the plurality of body locations the first and second body locations; presenting to the user a second display having a plurality of medical problems including a first medical problem, wherein the first medical problem determined to be associated with the physical examination; selecting from the plurality of medical problems the first medical problem; and storing a combination of the first and second body locations with the first medical problem as a medical finding for the first body system.

Another embodiment provides a system and method for detailing a medical finding. Such system and method may combine one or more prepared selections with on the fly created one or more selections for detailing a medical finding. On the fly created selections could have multiple input modes. For example, annotated text can be integrated with existing selection options.

Another embodiment of the invention is based on an electronic media, comprising a program for performing the methods of the invention. Another embodiment of the invention is based on a computer program, comprising computer or machine readable program elements translatable for implementing the methods of the invention.

The foregoing has outlined rather broadly the features and technical advantages of the present invention in order that the detailed description of the invention that follows may be better understood. Additional features and advantages of the invention which form the subject of the claims of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention and the advantages thereof, reference is now made to the following descriptions taken in conjunction with the accompanying drawings, in which:

FIG. 1 shows a prior art graphical user interface of an electronic medical chart.

FIG. 13 shows an exemplary graphical user interface of an electronic medical chart that may be used in an embodiment of the present invention to prompt a user to specify parameters for the selected procedure of FIG. 12.

DETAILED DESCRIPTION

Figure 1:
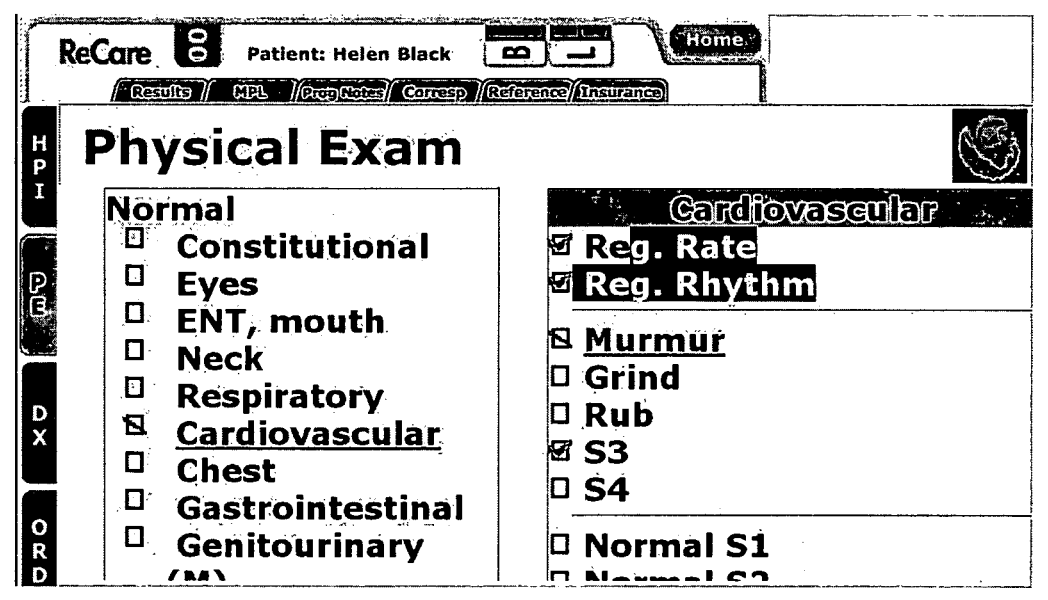
Figure 2:
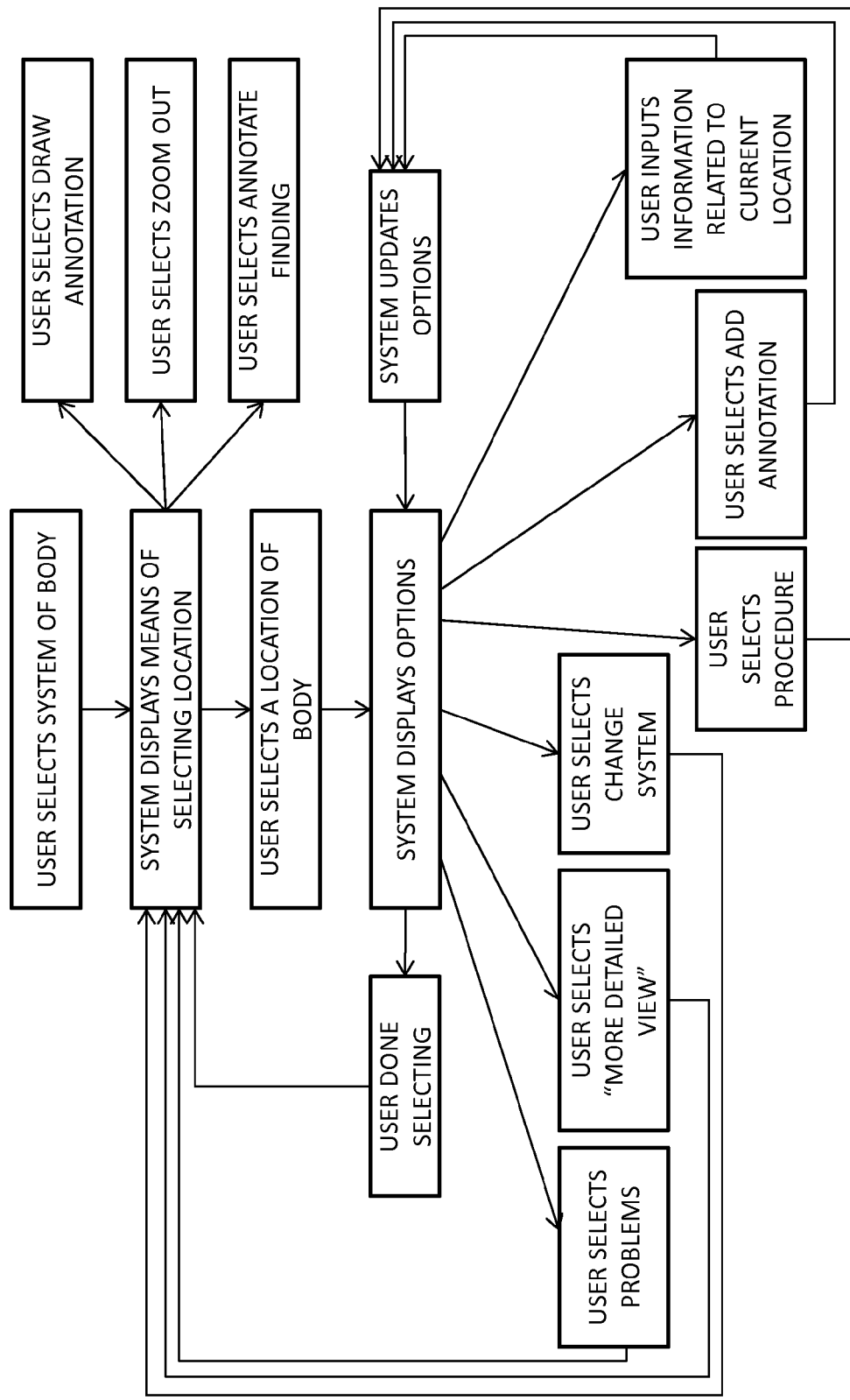
FIG. 2 is a flow chart showing an exemplary process for documenting medical findings according to one embodiment of the present invention.
Figure 24:
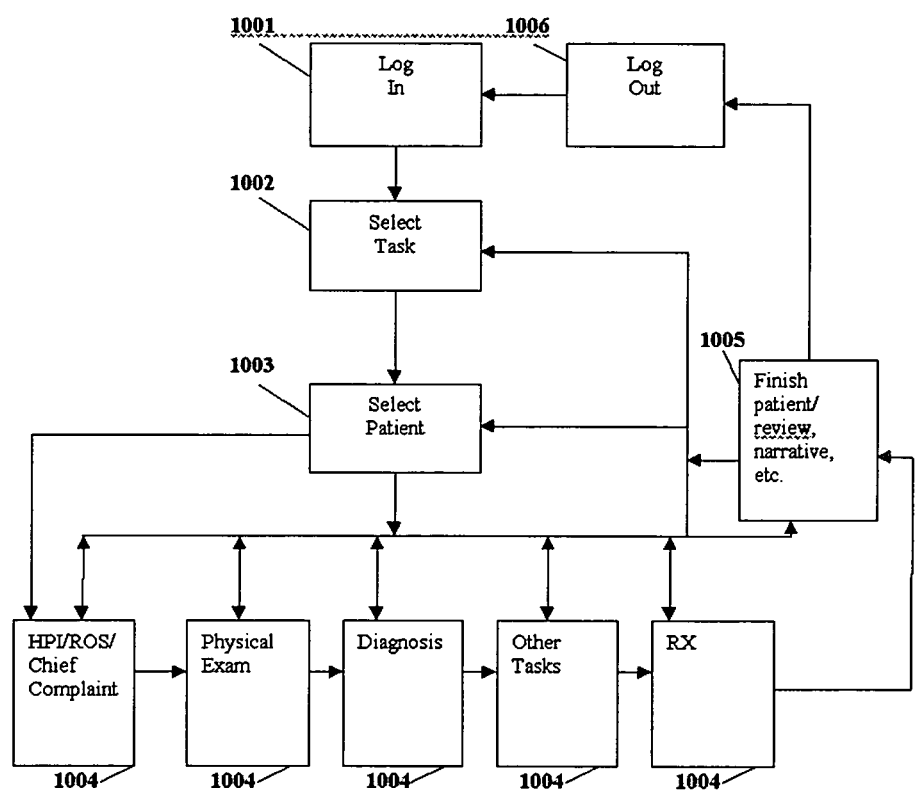
FIG. 24 is a flow chart showing how an exemplary physical exam medical system of the present invention using an exemplary method for documenting medical findings consistent with the present invention may be incorporated into an electronic medical record (EMR) system.

FIG. 1 shows a prior art graphical user interface of an electronic medical chart. FIG. 2 is a flow chart showing an exemplary process for documenting medical findings according to one embodiment of the present invention. With reference to FIG. 2 there is described the process by which a user documents findings associated with systems of the body. It is assumed at the beginning of this process that the user has logged in, has selected a patient with which to work, and has selected a task that requires documenting findings of the patient. FIG. 24 shown and discussed later illustrates one way of accomplishing this.

Referring to FIG. 2, to document findings, the user proceeds as follows:

1. User chooses a system of body (for example, musculoskeletal system, lymphatic system, or skin system). In one implementation, this step is accomplished by displaying a list of systems of the body on the screen of the user interface device and the user selecting a system using a pointing device such as a mouse or touch-screen. In some realizations, this step is omitted. The uncategorized problem embodiment and the complaint problem embodiment described below give examples of such realizations.

2. The system displays a means for selecting a specific location of the current region of the body. Commonly, the initial region is "whole body". However, note that this step may be returned to by later steps that have changed the current region of the body, so subsequent iterations of this step may be entered with different regions of the body representing the current region of the body.

Figure 3:
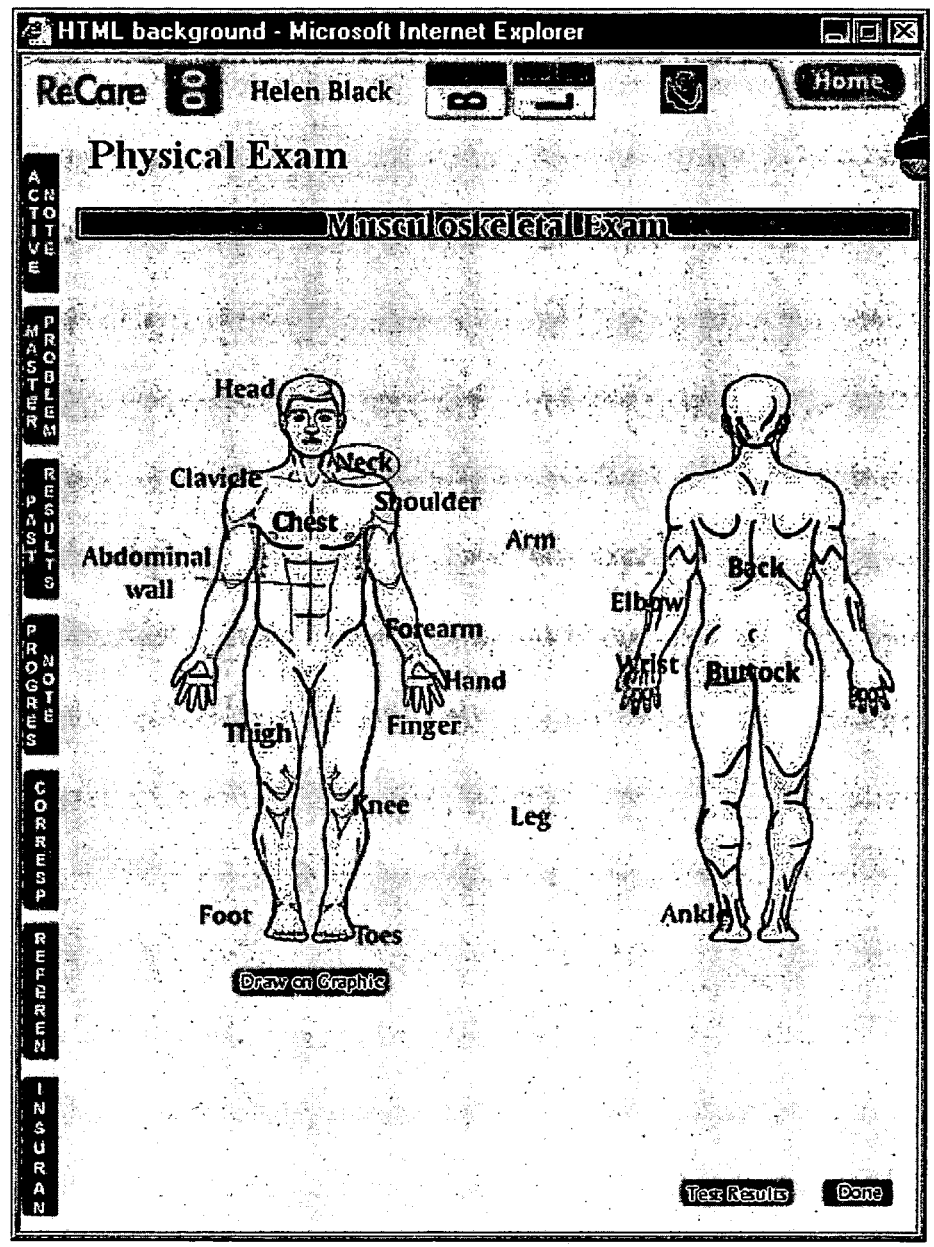
FIG. 3 shows an exemplary graphical user interface of an electronic medical chart that may be used in an embodiment of the present invention as location selection means.

FIG. 3 shows an exemplary graphical user interface of an electronic medical chart that may be used in an embodiment of the present invention as location selection means. In a preferred realization, the system displays schematic depiction of the current region of body that provides the ability to select particular locations (for example, as illustrated in FIG. 3, initially the current region is "whole body" and the system provides the ability to select the head location, neck location, shoulder location, arm location, forearm location, hand location, finger location, knee location, thigh location, toes location, foot location, abdominal wall location, clavicle location, elbow location, wrist location, buttock location, back location, and ankle location).

In one realization, the system displays a textual list of locations that may be selected. In an alternate realization, the system displays a schematic that also includes textual descriptors of some or all of the selectable regions.

In one realization, the schematic that is displayed for a region depends on the currently selected system of the body. For example, if the currently selected system of the body is the skin system, the display may schematically depict the surface of the skin in the selected region, but if the currently selected system of the body is the musculo-skeletal system, the display may schematically depict the muscles, bones, joints, and/or tendons below the surface of the skin.

In one embodiment, different graphic depictions are used depending on the age or developmental stage of the current patient. For example, a different image might be displayed to depict the "whole body" of a newborn than of a two-year-old child. In one embodiment, different graphic depictions are used depending on the gender of the patient.

3. User selects location of current region of body. In one implementation, this is accomplished by selecting the location by moving a mouse-controlled cursor to that location and clicking a mouse button. In one implementation, this is accomplished by touching the selected location on a touch-screen video display.

Figure 4:
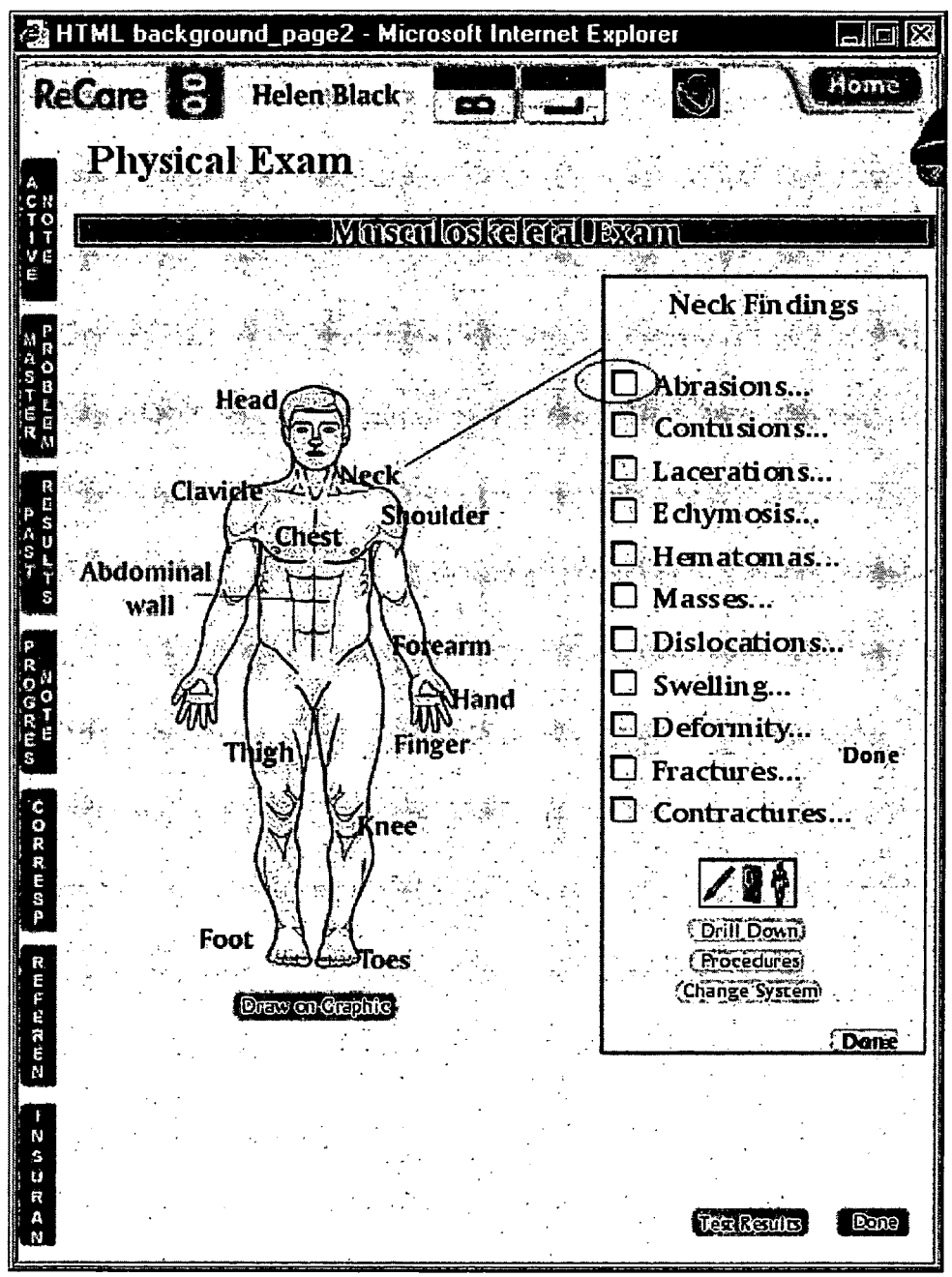
FIG. 4 shows an exemplary graphical user interface of an electronic medical chart that may be used in an embodiment of the present invention as problem selection means.

4. In response to the is selection, the system shows:
   a. a means of selecting findings at that location;
   b. a means of selecting to see a more detailed view of the selected body location (e.g., "drill down");
   zero or more of the following (different realizations may implement different subsets of these functions):
   c. a means of selecting of other systems of body;
   d. a means of selecting procedures that may be performed for the selected location for the current system;
   e. a means of selecting procedures that may be performed for the current set of inputted problems at the selected location;
   f. a means of selecting to add an annotation;

In one implementation, these elements are shown in a menu that appears near the selected location. An example of this is illustrated in FIG. 4. FIG. 4 shows an exemplary graphical user interface of an electronic medical chart that may be used in an embodiment of the present invention as problem selection means.

In one implementation, selection means (a) is realized by listing common problems for the current system of body and location (e.g., for "musculo-skeletal system of body"—list fracture, sprain, contusion, etc.) and, if not all common or important problems will fit in the designated region of the menu, a "other problems" entry which, when activated, displays additional problems in a hierarchical drop-down menu. In another implementation, this list of findings comprises recent findings entered by the user (e.g., a hot list). In another implementation, this list of findings comprises common problems given a plurality of factors chosen from the group of: patient's chief complaint, patient's gender, patient's age, patient's developmental stage, patient's active problems, patient's past problems, patient's current medications, patient's past medications, common findings entered by the user, recent findings entered by the user, and user's medical specialty.

In one implementation, selection means (b), (c), (d), (e), and (f) are each a menu entry that may be selected. In another implementation, selection means (c), (d), and (e) are implemented by displaying zero or more elements on the main menu and displaying the remaining elements (if any) on a hierarchical sub-menu that may be activated from the main menu. The next action of the system depends on which of these actions is chosen by the user.

Figure 5:
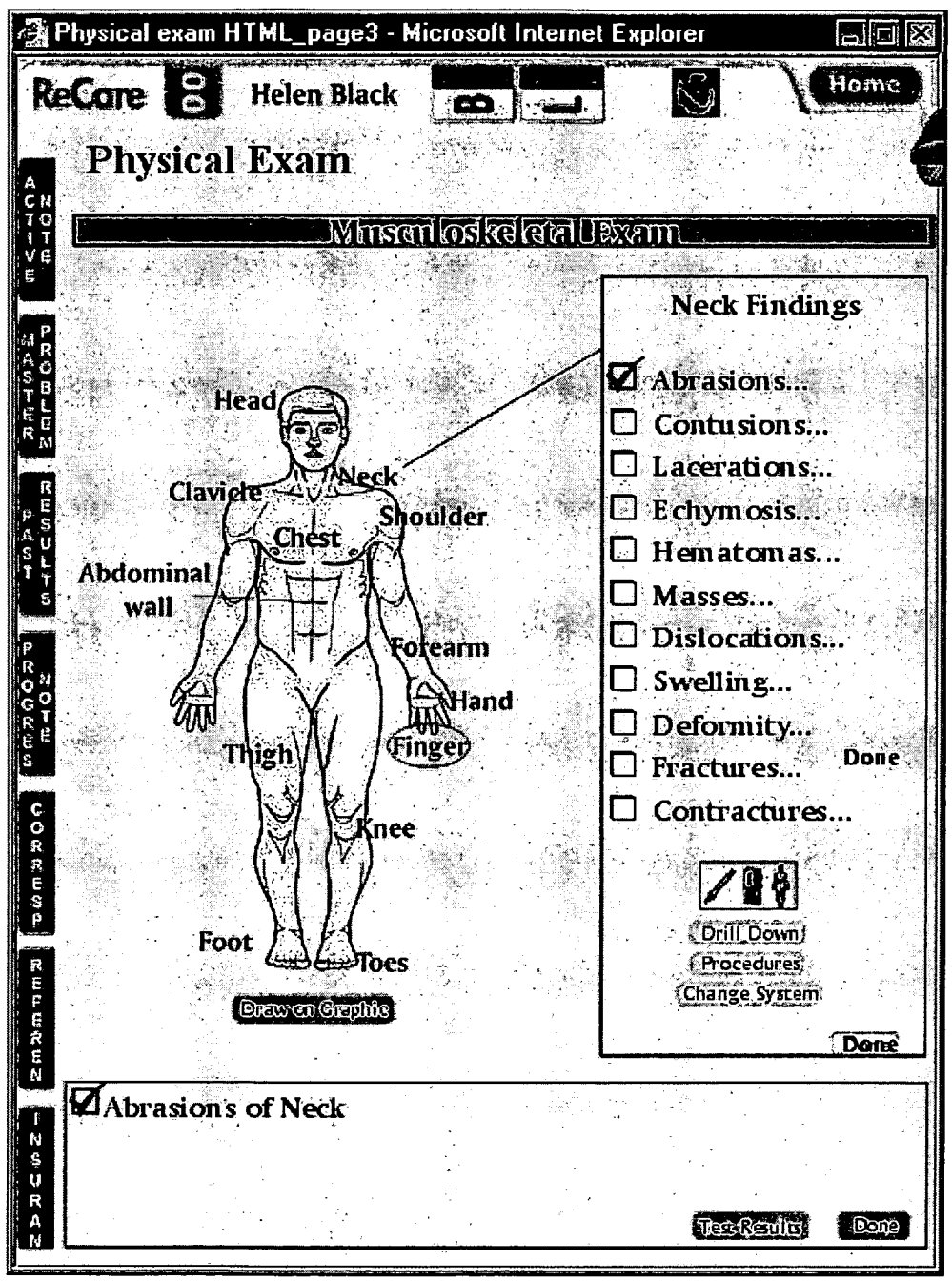
FIG. 5 shows an exemplary graphical user interface of an electronic medical chart that may be used in an embodiment of the present invention as select problem means.

5. If in step 4, the user selects option (4a), i.e.: User selects a plurality of problems for current system at the selected location. In one embodiment, the user activates the menu entry corresponding to a problem the user wishes to select. The system then adds the finding (with the selected problem at the currently selected location) to the set of findings for the current system. FIG. 5 shows an exemplary graphical user interface of an electronic medical chart that may be used in an embodiment of the present invention as select problem means.

In another embodiment, findings must not only be selected but must also have a state identified. This state may identify the polarity of a finding (e.g., problem is present, problem is not present, problem has not been assessed), or this state may identify the certainty with which an assessment has been made (e.g., problem is present, problem is suspected), or this state may represent a combination of these factors. For the purposes of this example, we will assume that the state is selected from the group PRESENT, NOT_PRESENT, and NO_FINDING_ENTERED.

In this embodiment, the state of the findings associated with each listed problem is initialized to a value. This value typically is NO_FINDING_ENTERED. Some systems may provide a means to initialize a group of specific findings to different values, for instance by allowing a user to indicate that a system is "normal", which implies that some specific findings within the system are initialized to PRESENT and other specific findings are initialized to NOT_PRESENT and the rest of the findings are initialized to NO_FINDING_ENTERED. For example, selecting "normal" for a musculo-skeletal exam might initialize the findings "Whole body full range of motion PRESENT", "Right hand cyanosis NOT_PRESENT", "Left hand cyanosis NOT_PRESENT", "Whole body swelling NOT_PRESENT", and all other findings "NO_FINDING_ENTERED". Such initialization is accomplished by storing the set of findings for each system that should be automatically entered if that system is noted to be "normal."

Regardless of the initial value, in this embodiment, the problem selection means displays a list of problems and the state of the problem for the current location. The state is displayed using graphical icons—e.g., an empty box for NO_FINDING_ENTERED, a box with a green check mark for PRESENT, and a box with a red back slash ("\") for NOT_PRESENT. The user may touch a state graphical icon and cause the state and icon to change, depending on its current state, from NO_FINDING_ENTERED to PRESENT, from PRESENT to NOT_PRESENT, or from NOT_PRESENT to NO_FINDING_ENTERED. As the state of a finding is changed, the system stores the resulting findings and states and also displays the resulting findings on the list of findings for the current system. The user may successively initiate state changes on multiple problem findings while the list is displayed.

Regardless of the embodiment for selecting elements or selecting the state of elements, in one embodiment the system may maintain a display of the set of findings that have been selected thus far at the location or across locations. If so, when an element is selected or its state changed from "NO_FINDING_ENTERED" to some other state, selected element is added to this list of selected findings. Conversely, if a finding is de-selected or its state changes to NO_FINDING_ENTERED, the system removes that finding from the displayed set of findings.

Regardless of the embodiment for selecting/changing the state of elements, in one embodiment once the user has made the desired selections/changes of zero or more findings, in one embodiment the user may click a "done" button to cause the means to be removed from the display. In another implementation, the immediately system removes the menu from the display when a single element is selected or changed without the need to explicitly select "done".

These two alternatives provide different trade-offs between the convenience of selecting multiple problems in the same location and of selecting a single problem per location. Some embodiments may provide one of the two options, other embodiments may implement both options and choose between the options based on (i) user-selected preference, (ii) user specialty, (iii) user patient population, (iv) chief complaint of the patient, (v) system of the body being document, or other factors.

After the user has updated zero more findings at the selected location using means such as those described above, the system redisplays the previously displayed region of the body (e.g., GOTO step 2). Note that by repeating steps 3, 4, 5 the user may efficiently document multiple findings at the same location of the body or locations near one another.

Figure 6:
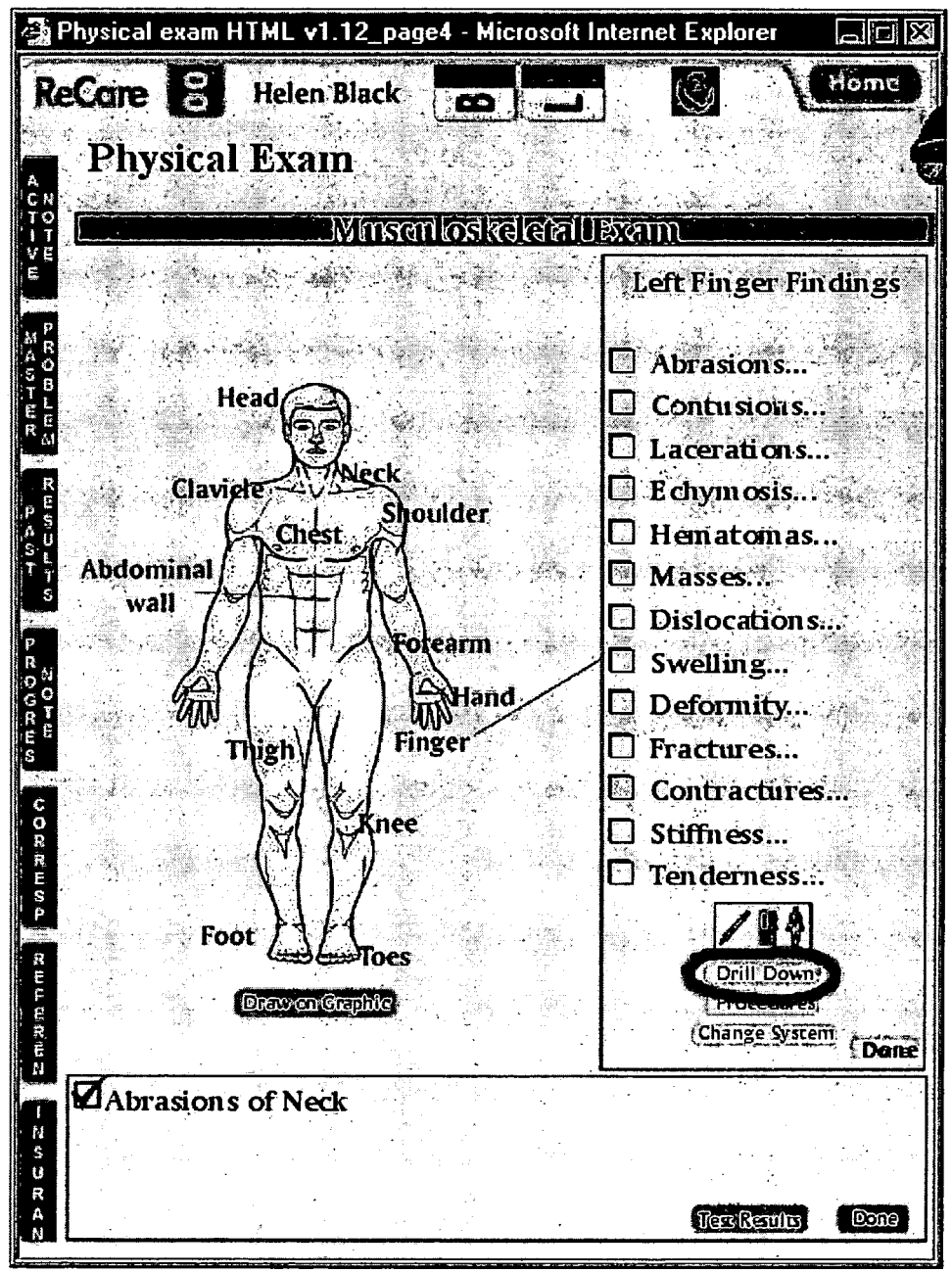
FIG. 6 shows an exemplary graphical user interface of an electronic medical chart that may be used in an embodiment of the present invention as drill down means.
Figure 7:
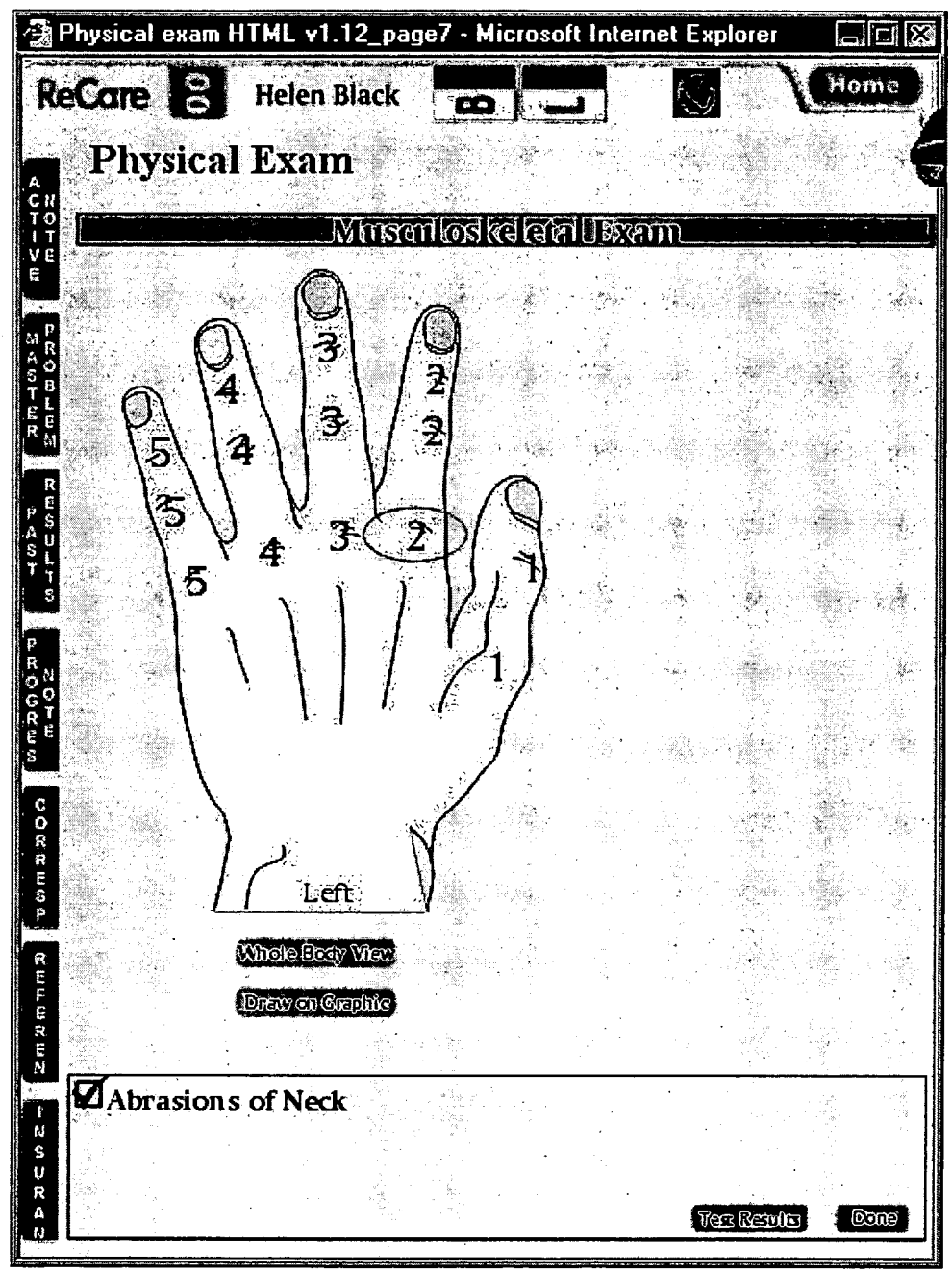
FIG. 7 shows an exemplary graphical user interface of an electronic medical chart that may be used in an embodiment of the present invention as drill down means to show more detailed view for selecting regions of the body that includes the selected location of the body.

6. If in step 4, the user selects option (4b) (i.e., User selects show more detailed view for selecting regions of the body that includes the selected location of the body). FIG. 6 shows an exemplary graphical user interface of an electronic medical chart that may be used in an embodiment of the present invention as drill down means. FIG. 7 shows an exemplary graphical user interface of an electronic medical chart that may be used in an embodiment of the present invention as drill down means to show more detailed view for selecting regions of the body that includes the selected location of the body.

The system makes the selected location of the body the current region of the body. The system then displays this region of the body (e.g., GOTO step 2). This function allows a user to "zoom in" to a more detailed region of the body in order to select locations with more precision. For example, during a musculo-skeletal examination, if before this step, the current region of the body is the right arm and hand, and the user selects the hand location and selects show more detailed view, the system would then display a graphic image of the hand that allows each finger joint to be individually selected.

Figure 8:
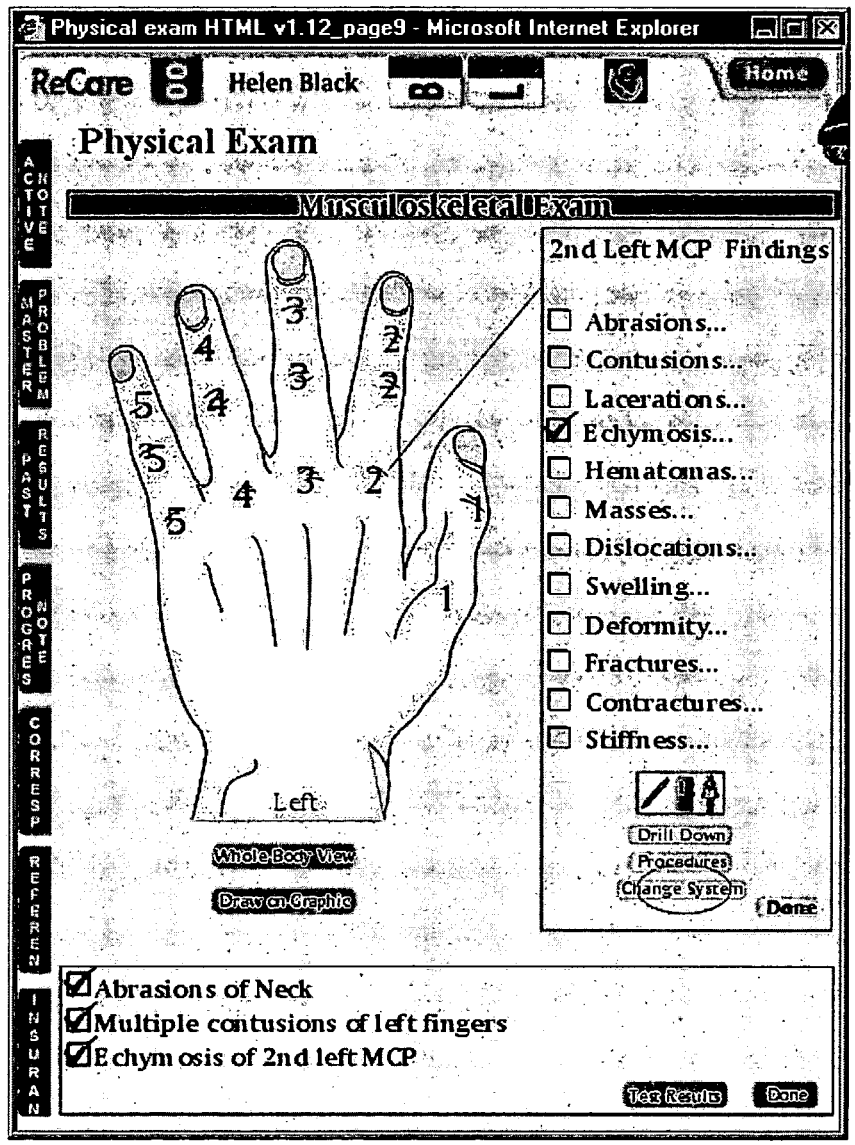
FIG. 8 shows an exemplary graphical user interface of an electronic medical chart that may be used in an embodiment of the present invention to change systems.
Figure 9:
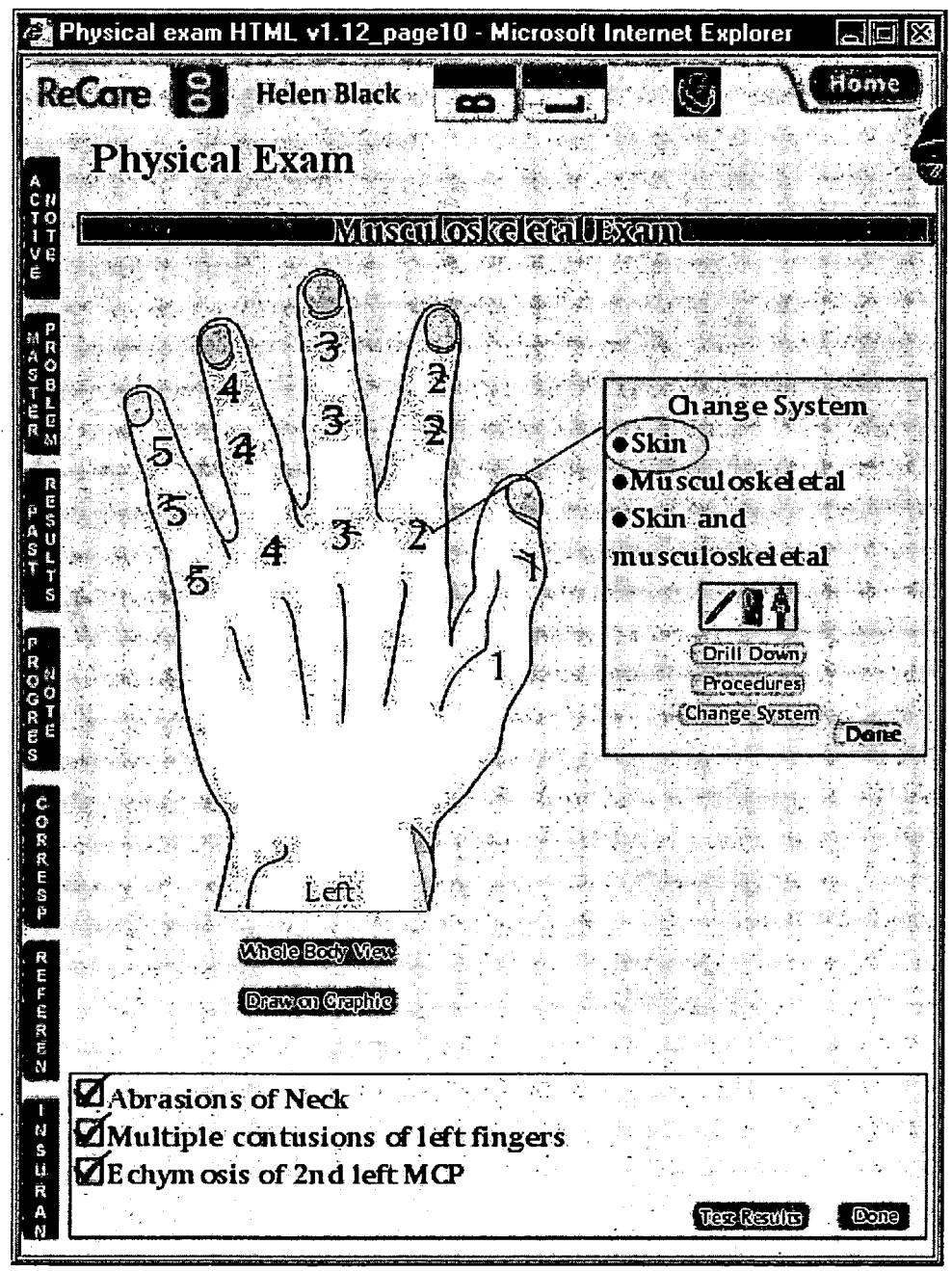
FIG. 9 shows an exemplary graphical user interface of an electronic medical chart that may be used in an embodiment of the present invention to list a set of common problems that spans multiple systems.
Figure 10:
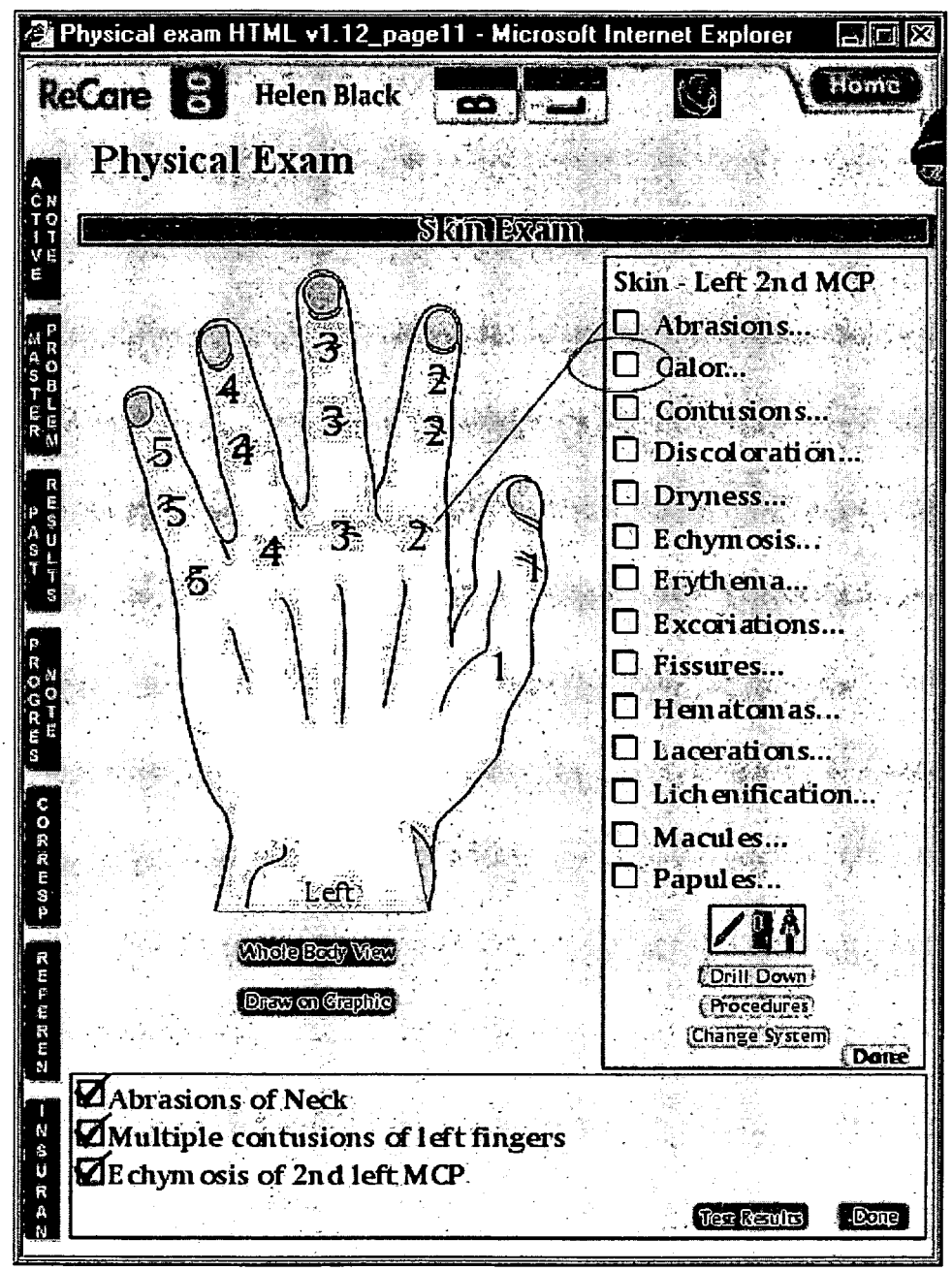
FIG. 10 shows an exemplary graphical user interface of an electronic medical chart that may be used in an embodiment of the present invention to list a set of problems that related to a patient's chief complaint or active problems.

7. If in step 4, the user selects option 4c (i.e., User selects a different system of the body). (This option step is optional—the system may organize problems using a manner other than by system of body; for example, by listing a set of common problems that spans multiple systems or by listing a set of problems related to a patient's chief complaint or active problems). FIG. 8 shows an exemplary graphical user interface of an electronic medical chart that may be used in an embodiment of the present invention to change systems. FIG. 9 shows an exemplary graphical user interface of an electronic medical chart that may be used in an embodiment of the present invention to list a set of common problems that spans multiple systems. FIG. 10 shows an exemplary graphical user interface of an electronic medical chart that may be used in an embodiment of the present invention to list a set of problems that related to a patient's chief complaint or active problems.

The system makes the selected system the current system. In one embodiment the system then transfers control to step 4 described above (the system displays a means for specifying one ore more selections/actions at the specified location). In a different embodiment, the system then transfers control to step 2 described above (the system displays the current region of the body). Note that this allows a user to quickly document multiple findings from different systems in nearby areas of the body. Note that by repeating steps 3, 4, 5, and 7 the user may efficiently document multiple findings at the same location of the body or locations near one another spanning multiple systems of the body.

Figure 11:
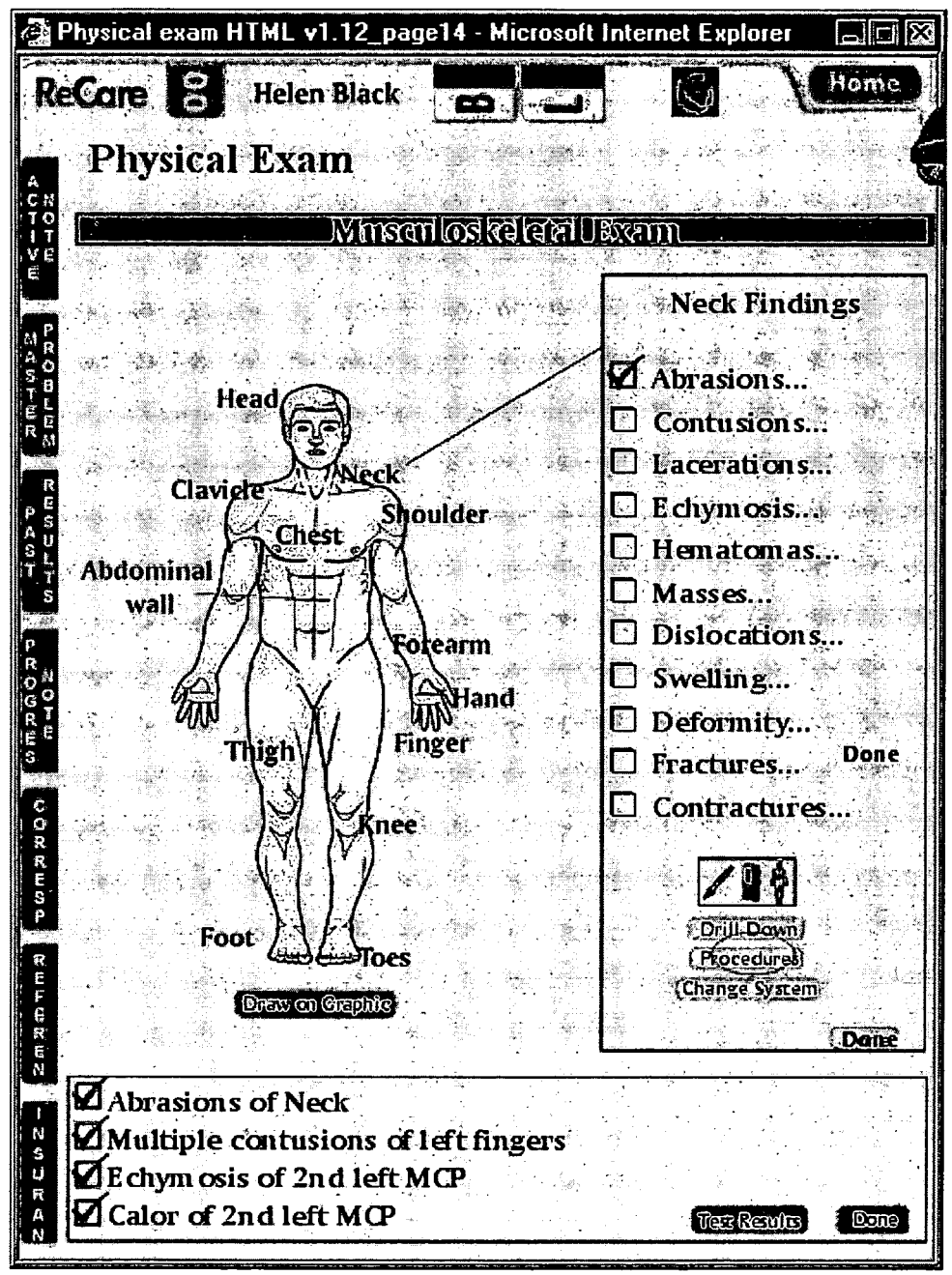
FIG. 11 shows an exemplary graphical user interface of an electronic medical chart that may be used in an embodiment of the present invention to select procedure.
Figure 12:
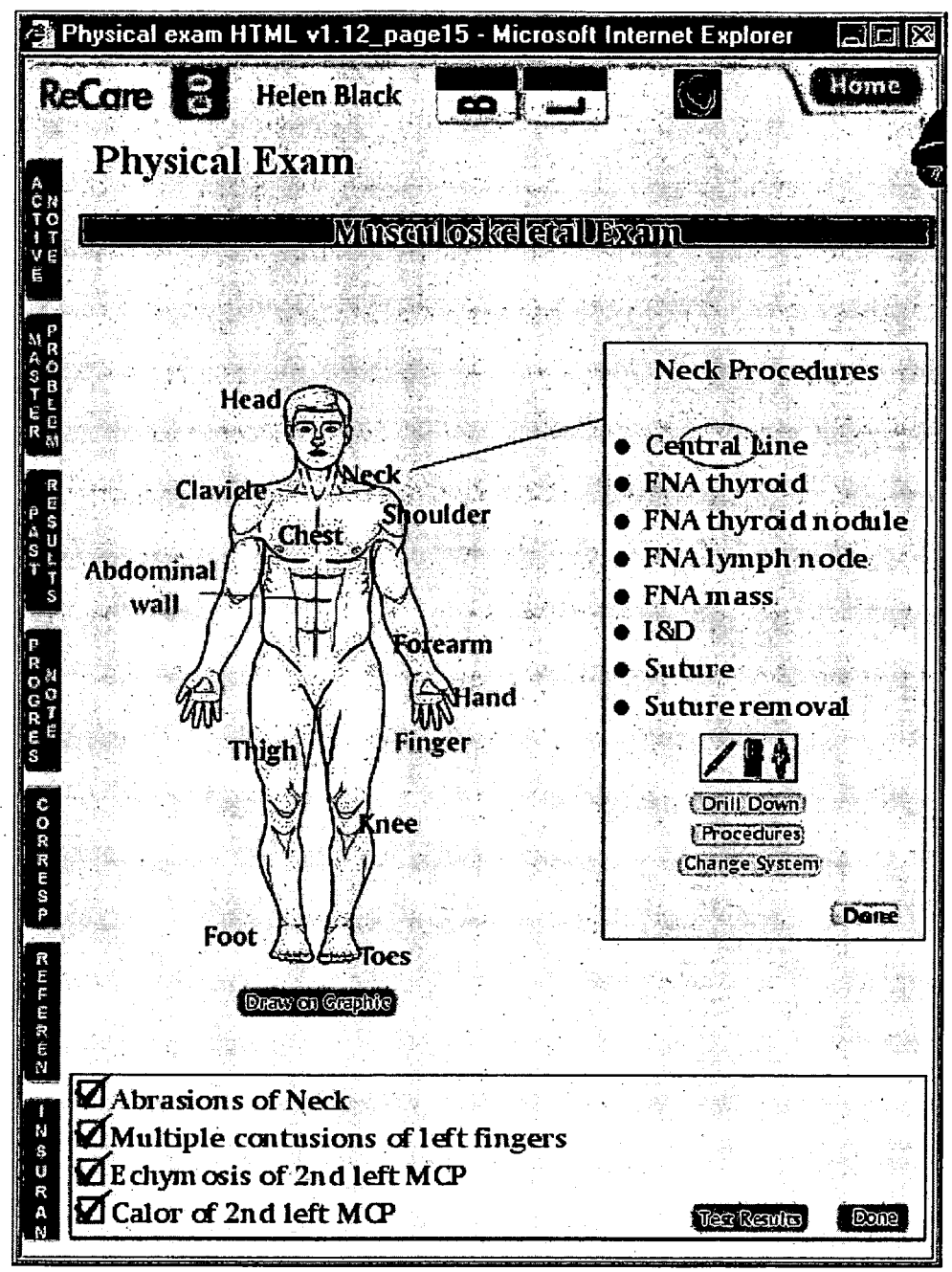
FIG. 12 shows an exemplary graphical user interface of an electronic medical chart that may be used in an embodiment of the present invention to select a procedure to perform from a list of multiple procedure for a region of a body.

8. If in step 4 the user selects option (4d) or (4e) (i.e., User selects a procedure to perform). FIG. 11 shows an exemplary graphical user interface of an electronic medical chart that may be used in an embodiment of the present invention to select procedure. FIG. 12 shows an exemplary graphical user interface of an electronic medical chart that may be used in an embodiment of the present invention to select a procedure to perform from a list of multiple procedure for a region of a body.

Figure 13:
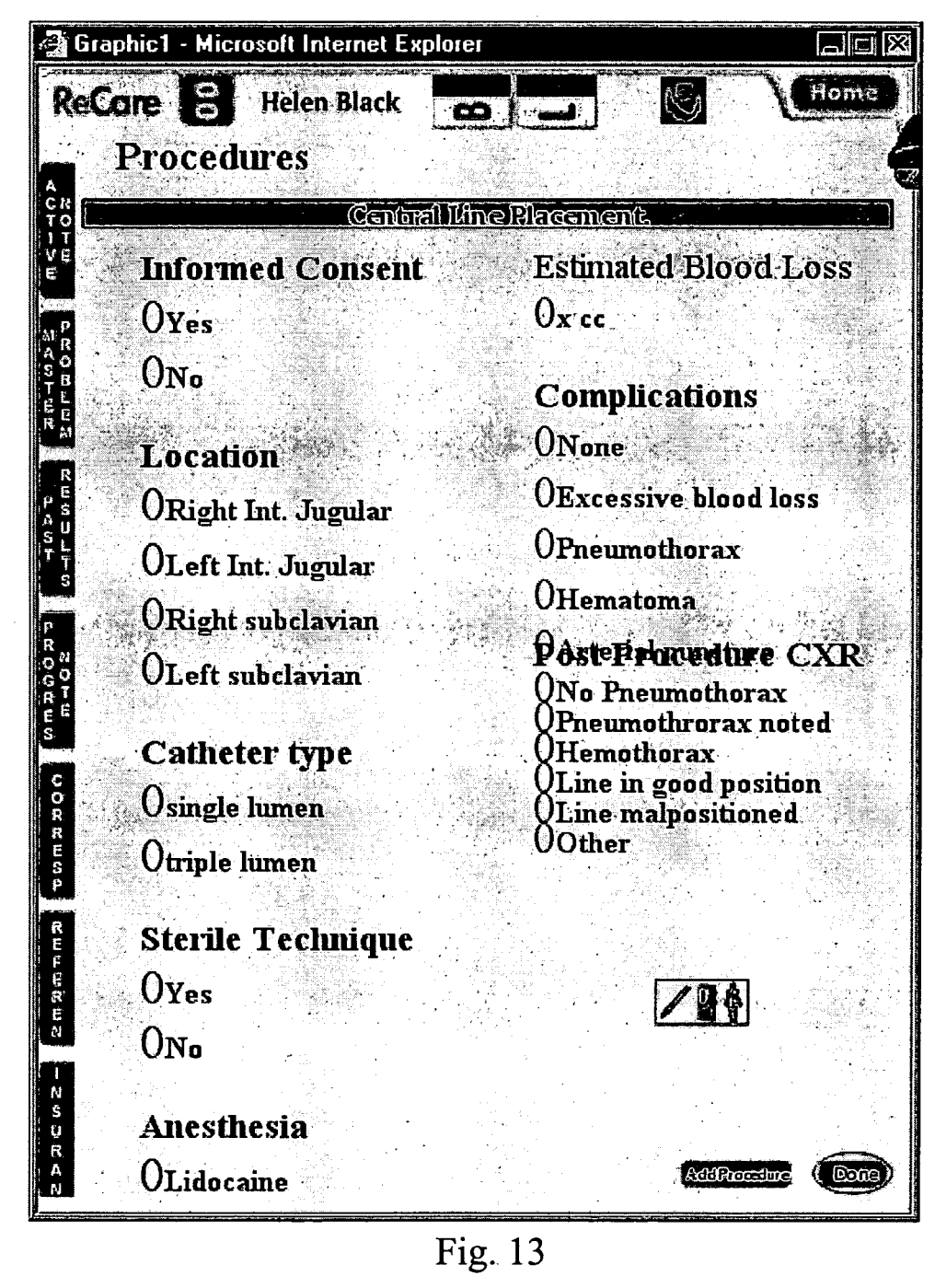

Optionally, the system prompts the user to specify parameters for the procedure. FIG. 13 shows an exemplary graphical user interface of an electronic medical chart that may be used in an embodiment of the present invention to prompt a user to specify parameters for the selected procedure of FIG. 12. The user specifies these parameters using textual input, selecting elements from lists, or other means that are known by that familiar with the art. The system adds the procedure (location, procedure) to the set of procedures ordered for the patient. The system then transfers control to step two described above (e.g., GOTO step 2)

9. If in step 4, the user selects option 4f (i.e., User selects to add an annotation). The system displays a means for entering additional information relating to the currently selected findings for the current location. These means may include methods for adding free-form information about a finding or set of findings such as audio recording, audio to text functionality, pen input capture, pen input to text, keyboard text entry, drawing pen input to draw a picture or add annotations to a standard template picture associated with the current location. The procedure to add a notation is described in detail in the subsection with reference to "Add Annotation".

When the user indicates annotation is complete, the annotation is stored by the system and is linked to the location. In one embodiment, the system displays an icon near the location in the location selection means indicating that an annotation for that location has been stored. In one embodiment, the system displays an icon or descriptive text in the display area of selected findings indicating that a notation has been stored at a specific location. The system then transfers control to step 2 described above (e.g., GOTO step 2). The remaining steps are optional.

10. After the user enters more information about the patient or enters orders about the patient, the system may reconfigure the list of options available to the user according to the means described in step 4 above. For example, if a user enters "swollen fingers" as a physical exam finding, the list of options would be amended to include "enter diagnosis: arthritis" for an elderly patient or the list of physical exam findings might be augmented to include more detailed or precise findings related to arthritis or joint swelling, or important differential diagnosis potential findings as calculated by a rules-based system such as Medcin would be highlighted on the list. In general, as the set of findings about the patient is edited, the system uses rules-based or learning based techniques to customize the options available to the user.

Figure 14:
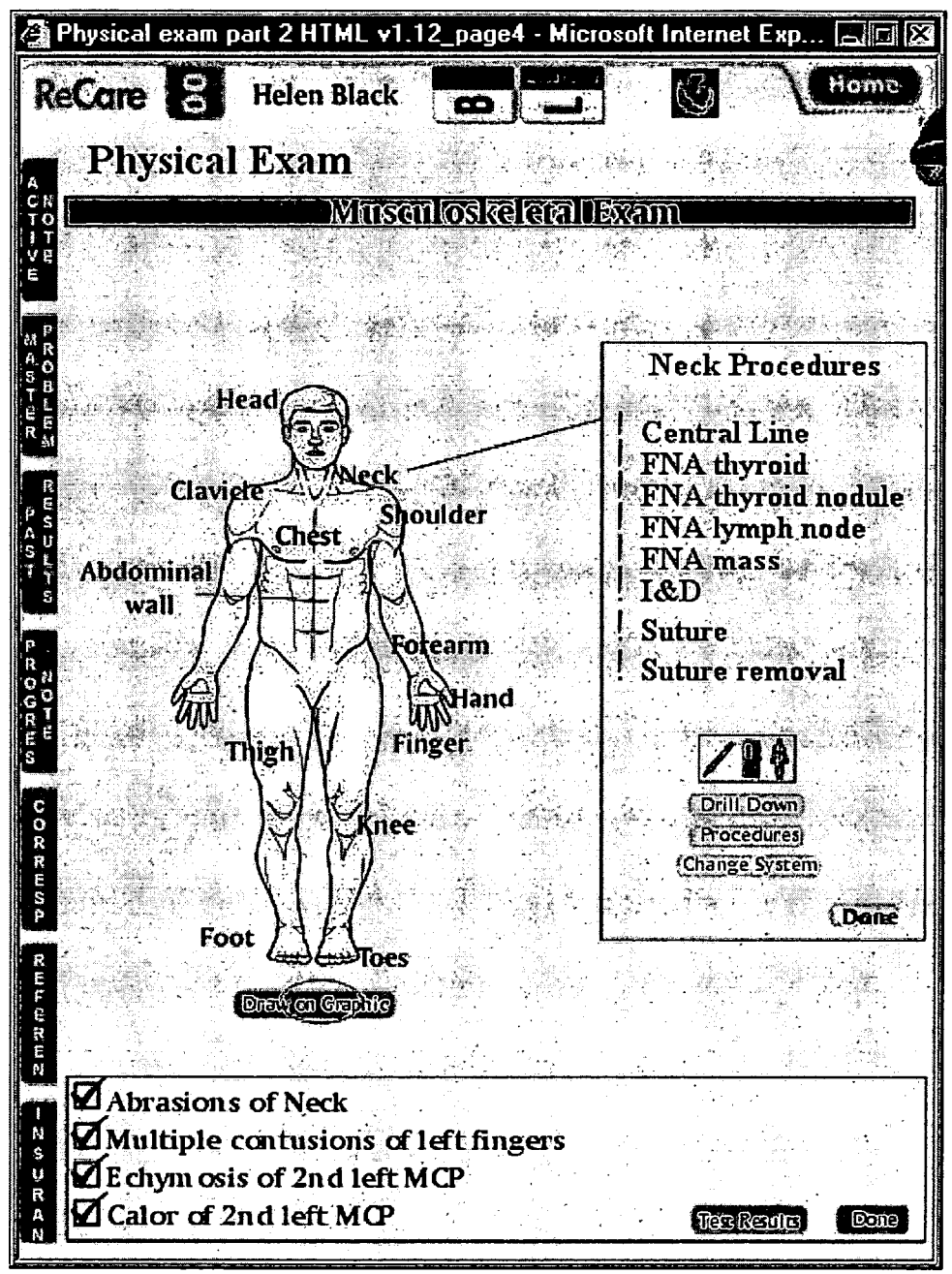
FIG. 14 shows an exemplary graphical user interface of an electronic medical chart that may be used in an embodiment of the present invention to select "draw" on a currently-displayed region and add a free-hand notation to the drawing.
Figure 15:
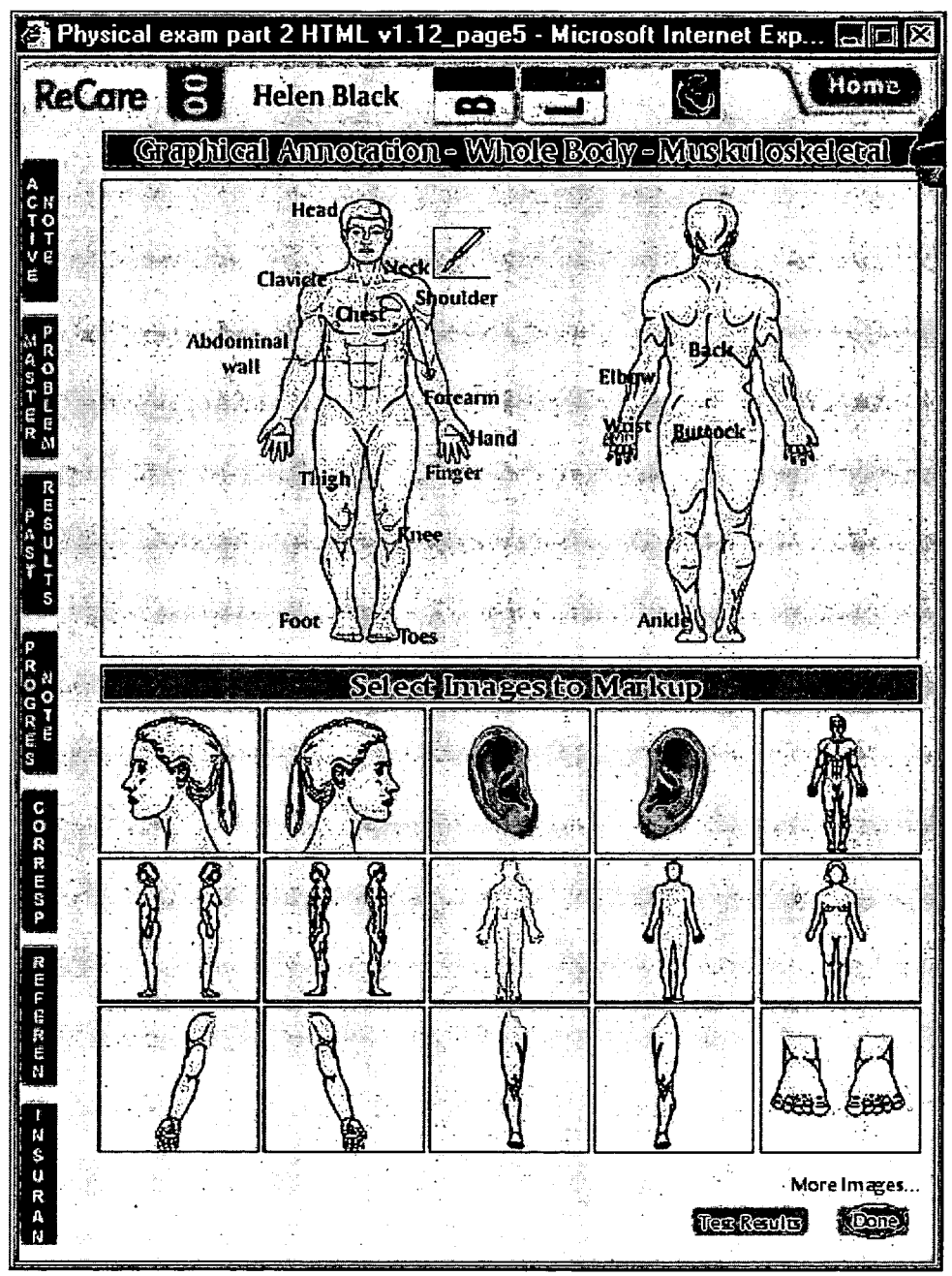
FIG. 15 shows an exemplary graphical user interface of an electronic medical chart that may be used in an embodiment of the present invention to select images to markup from a whole body for a graphical annotation of the current region of the body for the current system of the body.

11. At step 3, the user may select "draw" on currently displayed body region and add a free-hand notation to the drawing. This process is illustrated in FIGS. 14 and 15. FIG. 14 shows an exemplary graphical user interface of an electronic medical chart that may be used in an embodiment of the present invention to select "draw" on a currently-displayed region and add a free-hand notation to the drawing. FIG. 15 shows an exemplary graphical user interface of an electronic medical chart that may be used in an embodiment of the present invention to select images to markup from a whole body for a graphical annotation of the current region of the body for the current system of the body.

One embodiment of the system provides a means for drawing free-form graphic annotations on a graphical depiction of the current region of the body. In one embodiment, different graphic depictions are used depending on the current system of the body. For example, if the current system is "musculo system", the graphical depiction illustrates the muscles of the current region of the body. For example, if the current system is "skeletal system", the graphical depiction illustrates the bones of the current region of the body.

In one embodiment, different graphic depictions are used depending on the age or developmental stage of the patient. For example, a different image might be displayed to depict the "whole body" of a newborn than of a two-year-old child.

Figure 16:
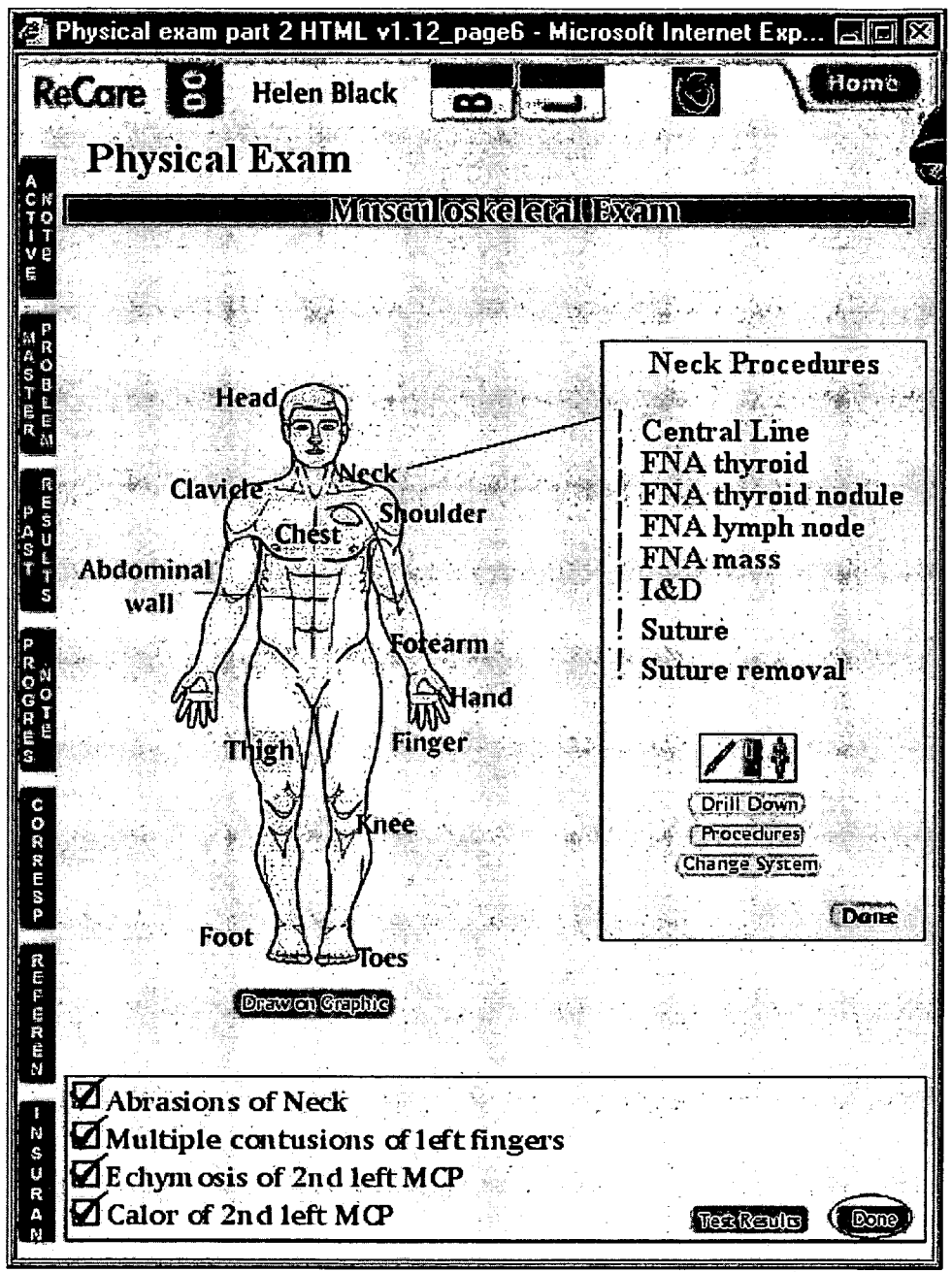
FIG. 16 shows an exemplary graphical user interface of an electronic medical chart that may be used in an embodiment of the present invention as a graphic navigation means with the graphic augmented to include drawn annotation.

In one embodiment, different graphic depictions are used depending on the gender of the patient. The system stores the drawing using a means such as "digital ink" that captures, displays, and stores the pixels selected by a pointing device such as a mouse, light-pen, or touch-screen pen. The system associates the drawing with the set of findings selected for the set of locations included in the currently displayed body part. In one realization, the system also provides a means for selecting a graphical depiction of a different region of the body on which to draw. When the user has finished drawing, the user selects "done drawing" and the system returns control to step 2 described above (e.g., the system displays the body navigation means). If the body navigation means is a graphic, in one realization that graphic may be augmented to include the drawn annotation as shown in FIG. 16. FIG. 16 shows an exemplary graphical user interface of an electronic medical chart that may be used in an embodiment of the present invention as a graphic navigation means with the graphic augmented to include drawn annotation.

12. Another action available to the user is to activates "add details to finding" for a finding. In one embodiment this option is activated at any step in the process by selecting a finding listed in the set of selected findings. For example, each element in that set may act as a "button" or "hyperlink" to the functionality described here. In one embodiment, this option is activated as an additional option in step 4 above by selecting a problem (which acts as a button or hyperlink to this functionality) from the displayed list of problems for the selected location.

Regardless of how this functionality is activated, the system then displays a means for adding details to the selected finding. This means is described in detail in subsection "Add Annotations below.

In one embodiment, upon completion of the adding of annotations, the display is updated to indicate that an annotation has been added to the specific finding that was annotated. For example, next to that finding an "annotation present" icon appears. In one embodiment, this annotation icon is different depending on the type of annotation (free text, voice, drawing, and additional selected options) that the annotation contains. Upon completion of the adding of annotations, control returns to the step that was executing previously to this step.

Figure 17:
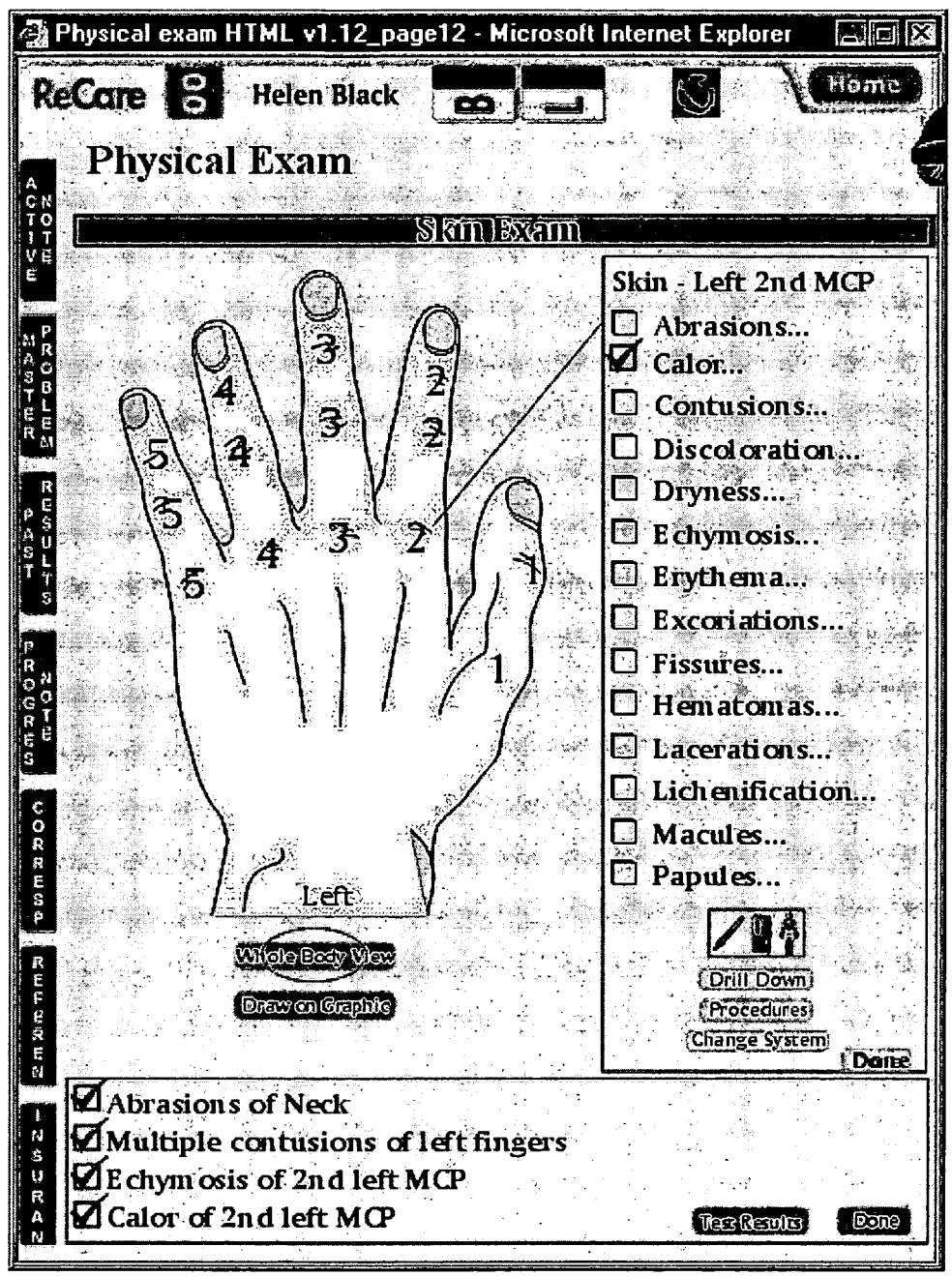
FIG. 17 shows an exemplary graphical user interface of an electronic medical chart that may be used in an embodiment of the present invention as a zoom in means.
Figure 18:
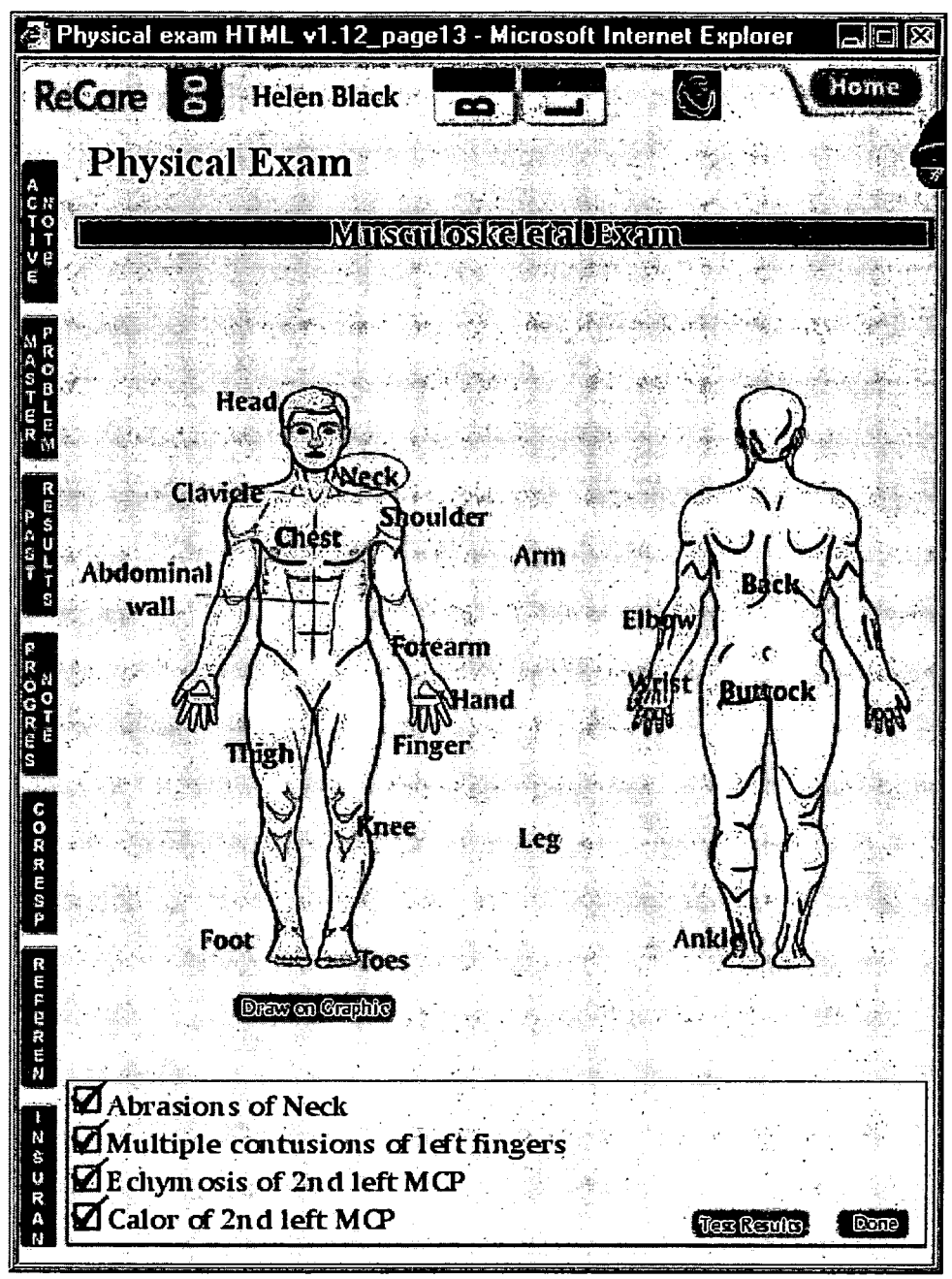
FIG. 18 shows an exemplary graphical user interface of an electronic medical chart that may be used in an embodiment of the present invention as a zoom out means.

13. When a "zoomed in" image is displayed, the user selects to "zoom out." In response to this user action, the system displays a view of the next higher broader region of the body and makes that broader region the current region of the body. This process is illustrated in FIGS. 17 and 18. FIG. 17 shows an exemplary graphical user interface of an electronic medical chart that may be used in an embodiment of the present invention as a zoom in means. FIG. 18 shows an exemplary graphical user interface of an electronic medical chart that may be used in an embodiment of the present invention as a zoom out means.

14. When a selection means for a particular part of the body is displayed, the user may select to toggle between "left/right" or "front/back" or both views or selection means. (Note: this step is not shown in the figure; the figure needs to be updated to show this step as an additional option from the "system display means of selecting location" box.

In response, the system changes the selection means to the corresponding location. For example, suppose the selection means displays the back of the right hand. By selecting the toggle functionality, the system could be made to switch directly to displaying the front of the right hand or the back of the left hand.

Add Annotation (or Details)

As described above, the user may choose to add an annotation to a location (e.g., an annotation that applies to all findings in the location, or that describes general context for evaluating that location) or add an annotation to a specific finding. This technique for detailing a location or finding works as follows. First, the user activates the option to detail a finding or location as described above. In response, the system displays a means for annotating the selected finding.

Different embodiments may provide different subsets of options for documenting the finding or location in greater detail. Such options include: (Note: master list here referred to from below) (a) recorded voice annotation, (b) voice input to a voice recognition computer program such as Dragon System's Dragon Naturally Speaking Medical Suite, (c) freehand drawing, (d) free hand annotations on a graphical depiction of the current location of the body, (e) selecting from a list of pre-generated annotations, (f) free text annotation input via a keyboard, virtual on-screen keyboard, or other text input means known to those trained in the art of computer system I/O, (g) recording a "digital ink" handwritten note, (h) an electronic photograph of the location on the patient, (i) an electron photograph of the location on the patent annotated with digitally captured free-hand drawings by the user, (j) selecting zero more detailed findings related to or modifying the base finding being annotated, (k) setting a "state" of "present"/"not present" for detailed findings related to the base finding being annotated, (l) text entered via a handwriting recognition system such as a restricted handwriting recognition system such as Palm, Inc's Grafitti system, or a general handwriting recognition system.

Figure 19:
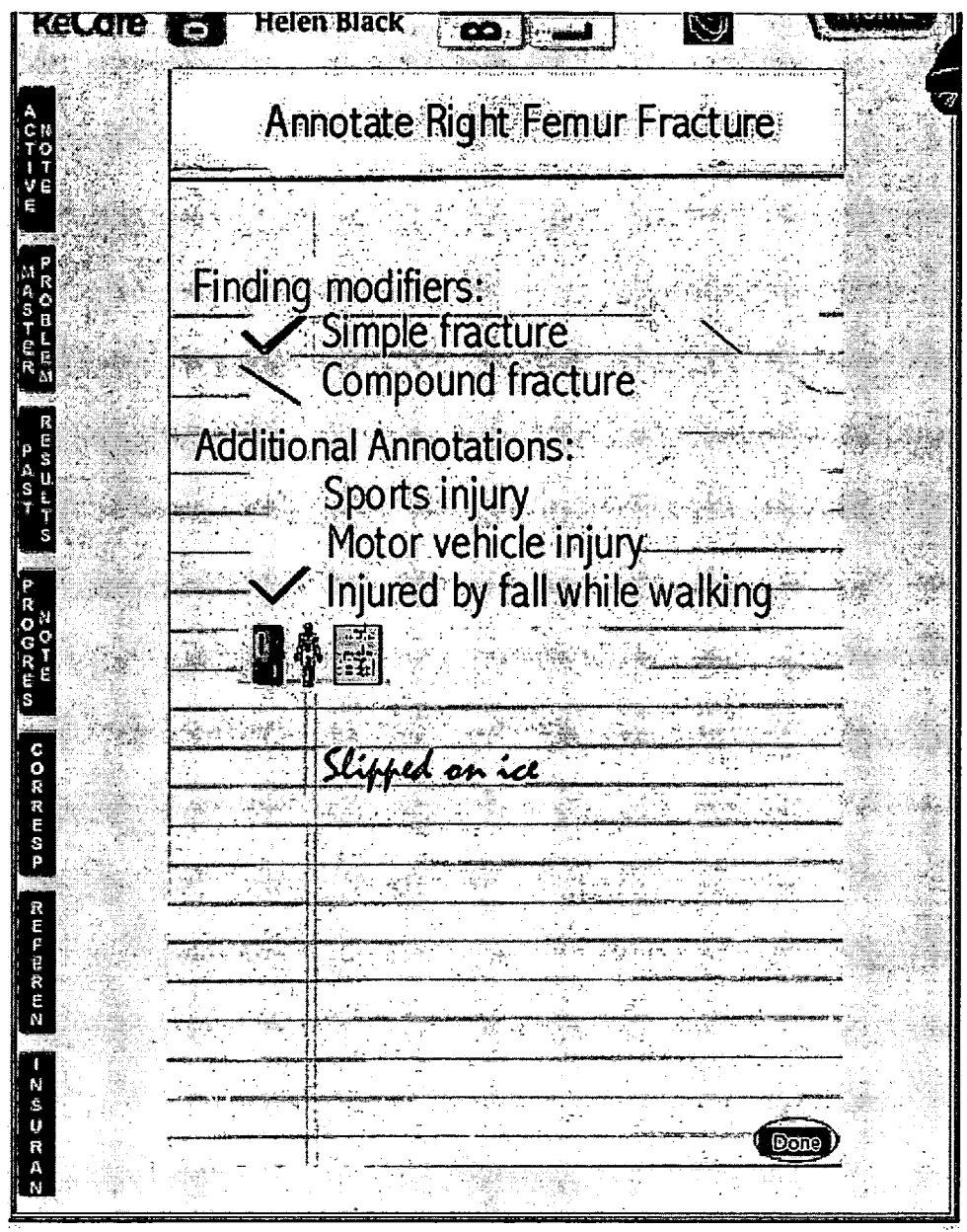
FIG. 19 shows an exemplary graphical user interface of an electronic medical chart that may be used in an embodiment of the present invention to provide a variety of options.

FIG. 19 shows an exemplary graphical user interface of an electronic medical chart that may be used in an embodiment of the present invention to provide a variety of options. FIG. 19 illustrates the embodiment that provides options (a), (d), (e), (k), and (l). The workings of methods (a), (c), (f), and (g) will be apparent to those skilled in the art. Each of these methods captures and stores simple input (text, voice, or pixels) using standard input/output and storage means.

The workings of methods (b) and (l) are similar to one another. In each, analog "real world" input (e.g., voice or handwriting) is first captured by computer hardware (e.g., microphone or touch screen) and converted to digital form. Hardware for such conversion is commonly included on commodity portable computer devices. The input is then fed to a software system for converting the input to text. Software modules for converting voice to text are available from a number of vendors including Dragon Systems and International Business Machines, Corporation and need not be described in detail here. Software modules for converting handwriting to text are available from a number of vendors including Palm Inc., CIC, Paragon Software, and Apple, and need not be described in detail here. The resulting text may then be stored as an annotation. Optionally, the original digitized input may also be stored (either in complete form or in compressed form).

The workings of method (d) for free hand annotation on a graphical image are to first retrieve from storage a graphical image of the current region of the body. In one embodiment, this image is selected from a group of images of the region of the body to correspond to the patient's gender, the patient's age or developmental stage, the system of the body currently selected, or a combination of these factors. The image is then displayed to the user, and the user "draws" on the displayed picture using a pointing device such as a mouse or pen/touch-screen input device. The drawing is stored as a series of (x, y) coordinates, each element in the series corresponding to a pixels selected on the screen by the pointing device. In addition, the later retrieval can retrieve both the graphical image and the annotation drawing and thereby display both of them together.

The workings of methods (h) and (i) for photographic annotation are similar to one another. In embodiments that include either or both of these options, the hardware system includes a digital camera either integrated with the terminal used by the user (as in commercially available web cameras or integrated into the terminal device as in the Sony Picturebook C1) or provided as a separate device connected to the terminal via a network. The user activates the camera to take a picture and the system stores this picture in the patient's medical record. The system then displays this picture. If the system provides a means for annotating this picture, the system allows the user to annotate the picture using free-hand drawing in the manner described for the schematic annotation means described above.

The workings of methods (e), (j), and (k) for selecting pre-generated annotations or detailed findings from a list are similar to one another. In one embodiment, a system administration user pre-generates lists of elements to be displayed, with the list to be used as selected by the finding or body location being annotated. In another embodiment, the medical user generates the list via a separate data-entry process in which the user types in or selects the desired list elements. In another embodiment, the system automatically assembles the list by selecting recent or common free-text annotations entered by the user. In another embodiment, the system automatically assembles the list by selecting recent or common free-text annotations entered by a group of users.

Regardless of the method used for generating the pre-generated annotations, these lists may comprise zero or more elements, each element comprising a unique identifier and a descriptor. The descriptor may describe annotations of different types, including (i) common textual annotations for the finding or location (e.g., for "arm fracture," common annotations might include "patient was riding a bicycle", "patient was skateboarding", "patient was involved in motor vehicle accident", "patient fell when walking", and "patient was playing sports"), (ii) detailed findings that correspond to common detailed findings for the finding or location (e.g., for "arm fracture" common detailed findings might include "wrist pulse present" or "dislocation present"), or (iii) modifier findings that modify the base finding being annotated (e.g., for "arm fracture" common modifiers might include "simple", "compound").

When a user selects to annotate a location or a finding, the system displays the pre-generated list of annotations corresponding to that location or finding. For methods (e) and (j), the system provides a means such as "check boxes" to allow the user to select zero or more of the displayed elements. In these methods, for each element selected the system stores the unique identifier of the annotation or finding selected. For method (k), the system provides a means for selecting the state (e.g., "PRESENT", "NOT_PRESENT", or "NO_FINDING_RECORDED") for zero or more of the elements. For this method, the system stores the state of all findings whose state differs from "NO_FINDING_RECORDED".

After completing the input as described above, the user indicates that the annotation is complete (in one embodiment, by clicking a button labeled "Done"). The system then returns to the place from which this method was called. In one realization, the system displays an icon next to the finding or location that has been annotated to indicate that additional details are available. In one realization, the system displays the annotations in full form.

Uncategorized Problem Embodiment

The System problem embodiment above describes a case where problems are grouped by system of the body. In another embodiment, problems are not grouped. The step of selecting a system is omitted, the option to change systems is omitted, and the list of problems displayed for a location may span multiple systems of the body.

Complaint Problem Embodiment

The system problem embodiment describes a case where problems are grouped by system of the body. In another embodiment, sets of problems likely to occur for patients with a specific chief complaint are collected into a group, and each type of problem may appear in zero or more groups regardless of the system of the body these problems are associated with. For example, the group associated with the chief complaint "motor vehicle accident" might include common problems for motor vehicle accident victims—fractures, bruises, lacerations, amputation, etc. In this embodiment, the step of selecting a system is omitted. Instead, the user or a different user such as a receptionist or the patient enters the chief complaint or the system retrieves a previously entered patient's chief complaint when the user selects the patient as the current patient. Regardless of the means for selecting the chief complaint, in this embodiment, the list of problems displayed when a location is selected includes problems associated with the chief complaint but that may span multiple systems of the body.

A simple way to realize this is to provide complaint-specific templates where each template provides a list of problems that should be presented for a given (location, chief complaint) pair. In addition to making the list of problems complaint specific, the list of available orders or other information may be selected from complaint-specific templates. FIG. 24 illustrates the flow of an electronic medical record system in which the user selects the chief complaint for a patient and then performs a physical exam. (This figure is described in detail below).

User Specialty Embodiment

The system problem embodiment describes a case where problems are grouped by system of the body. In another embodiment, sets of problems commonly treated by a particular practitioner are collected into a group. For example, the group associated with an internist specializing in geriatric care might include common problems for elderly patients—cyanosis, swelling, joint pain, fracture, etc. In this embodiment, the step of selecting a system is omitted. In this embodiment, the list of problems displayed when a location is selected includes problems associated with the user specialty or practice but that may span multiple systems of the body.

In this embodiment the step of selecting the system of the body may be omitted—the default "system" is the set of findings associated with the practice. But the option to switch systems may be retained to allow the user to switch from documenting "common problems for the practice" to documenting findings for a specific system thereby providing additional system findings that may be selected that do not appear on the "common problems" list Template Selection Embodiment The system problem embodiment describes a case where problems are grouped by system of the body. In another embodiment, clinically related sets of problems, orders, and other information are collected into groups called templates, where each template specifies a set of problems orders, and other information to be presented as options at specified locations of the body. In addition, each template specifies rules under which the template should be selected. In one embodiment, these rules comprise a Boolean function of the data in the EMR record concerning the current patient—if the rules match, the specified template is used to provide options for the location.

Dynamic Selection Embodiment

The system problem embodiment describes a case where problems are grouped by system of the body. In another embodiment, clinically related sets of problems, orders, and other information are dynamically collected into groups of a set of problems, orders, and other information to be presented as options at a specified location of the body. This selection is accomplished dynamically—as new findings are entered about the patient, new collections are generated. This generation is accomplished using a rules-based decision support system such as that provided by Medcin. Alternatively, this generation may be accomplished using a learning means such as neural nets, which use history to generate commonly selected elements given a configuration of inputs.

Repeat Past Entries Embodiment

A key efficiency issue for some medical practitioners is entering large numbers of related findings for a set of areas of the body. For example, a reumotologist might document the function of each joint on both hands of a patient. In such a case, many of the entries would simply be to document a finding of "normal" function. In many cases, the doctor will be required to document the same "normal" findings on multiple occasions. This embodiment of the system provides a means for efficiently documenting such repeated episodes. The list of options may include one or more "repeat findings from DATE" elements where "DATE" is replaced with a reference to an earlier examination.

The user may select that option to efficiently enter data from the past exam into the current exam. In particular, when that entry is selected, the system copies the findings at or hierarchically below the selected location from the selected date to the current exam. These findings appear on the summary of current findings screen and may be updated by the user.

Simultaneous Display Embodiment

Figure 20:
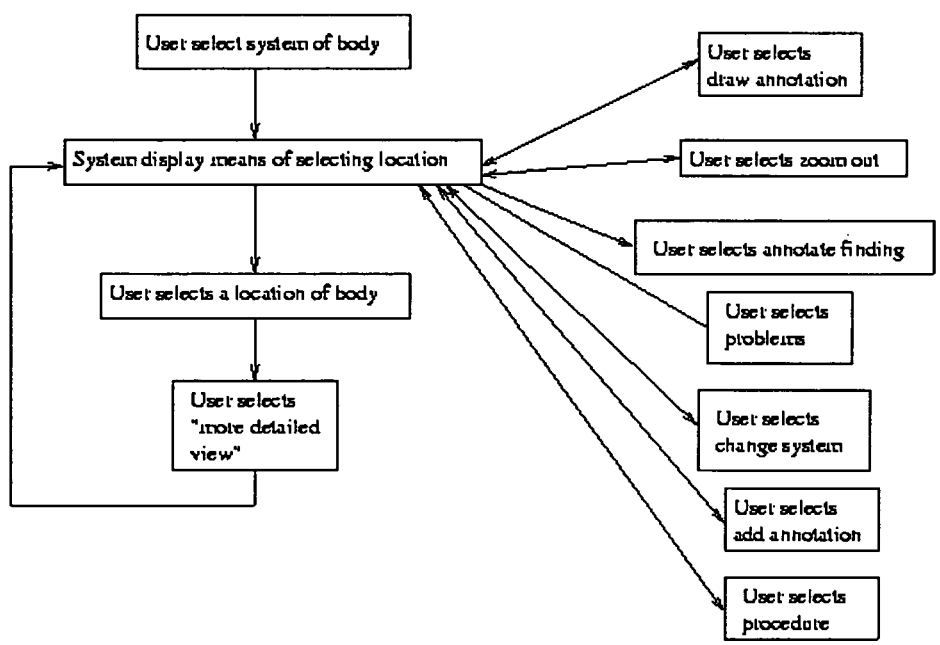
FIG. 20 is a flow chart illustrating the flow of an electronic medical record (EMR) system in which a user selects a chief complaint for a patient to perform a physical exam.

FIG. 20 is a flow chart illustrating the flow of an electronic medical record (EMR) system in which a user selects a chief complaint for a patient to perform a physical exam. With reference to FIG. 20, a simultaneous-flow shows an alternate embodiment of the method described in FIG. 2. In this embodiment, the system always displays the list of options that operate on the currently displayed region rather than requiring the user to select a location and causing options to be displayed for that selected location. For example, if the currently displayed region is "whole body", problems displayed as an option might include "pallor" or "rash" and selecting one of those problems would enter the finding "whole body pallor" or "whole body rash." Similarly, selecting "procedures" would cause the system to display a means of selecting from among procedures associated with the whole body region.

In the embodiment described here, a user may still select a particular location to "drill down" to that location. An alternate embodiment would be to include "drill down" in a list of actions, and require the user to select a location after selecting the drill down action.

Mixed Display Embodiment

It will be apparent to those skilled in the art that the organizations described in FIGS. 2 and 20 may be combined to provide a subset of options available as actions on the displayed region and a subset of options available as actions on a selected location. These subsets may overlap—e.g., the same option may be made available for both a displayed region and a selected location.

System Architecture

Figure 21:
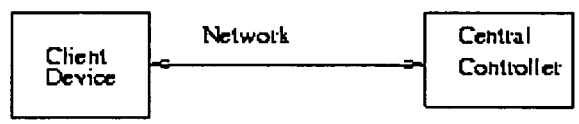
FIG. 21 is a high-level block diagram of the architectural components of an exemplary physical exam medical system having a client device and a central controller.

FIG. 21 is a high-level block diagram of the architectural components of an exemplary physical exam medical system having a client device and a central controller. The system architecture of a first embodiment of the apparatus and method of the present invention is illustrated with reference to FIG. 21. As shown in FIG. 21, the apparatus of the present invention comprises a client device and a central controller. Each node is connected via a network connection using a wireless radio frequency network such as provided by the Orinco 802.11 WAVELAN PCMCIA card or the Bluetooth standard. Connections may also be established by a wired network such as an Ethernet or token ring network, by cellular, Personal Communication Systems ("PCS"), microwave, Internet, infrared, or satellite networks.

In a second implementation, the client device and the central controller are one and the same machine, and communication between the modules is accomplished through the memory system of that machine. Using the above components, the present invention provides a method and apparatus to document medical findings and to issue treatment orders.

Figure 22:
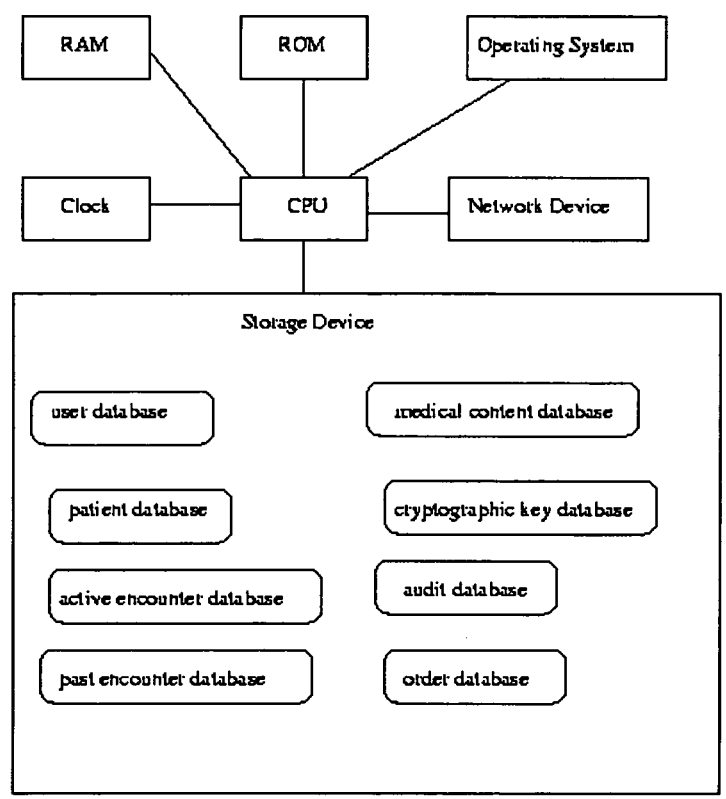
FIG. 22 is a block diagram of the central controller of FIG. 21 with exemplary details.

FIG. 22 is a block diagram of the central controller of FIG. 21 with exemplary details. As shown in FIG. 22, the central controller includes a central processor (CPU), a RAM, a ROM, a clock, an operating system, a network interface, and a data storage device.

A conventional personal computer or computer workstation with sufficient memory and processing capability may be used as central controller. In one embodiment, it operates as a web server, receiving requests from the client device and sending replies to client device Central controller must be capable of high volume transaction processing, performing a significant number of mathematical calculations in processing communications and database searches. A Pentium microprocessor such as the 100 MHz P54C commonly manufactured by Intel Inc may be used for CPU. This processor employs a 32-bit architecture. Equivalent processors include the Motorola 120 MHz PowerPC 604 or the Sun Microsystems 166 MHz Ultra SPARC-I.

Data storage device may include hard disk magnetic or optical storage units, as well as CD-ROM drives, DVD drives, or flash memory. Data storage device contains a plurality of databases used in the processing of a patient medical encounter, including a user database, a patient database, an active encounter database, a past encounter database, a medical content database, a cryptographic key database, an audit database, and an order database. In a preferred embodiment, database software such as Oracle 7, manufactured by Oracle Corporation, is used to create and manage these databases.

The user database maintains data on users with fields such as identifying number, name, public/private key information, password, type of user (e.g., doctor, nurse, technician), specialty, and preferences. The patient database maintains data on patients with fields such as patient identifying number, name, age, gender, race, address, contact information (e.g., phone number, e-mail address) active medical problems, past medical problems, current medications, past medications.

The active encounter database maintains data about in-progress sessions where a user is documenting the medical conditions of a patient. Each active encounter includes fields such as encounter identifying number, user identifying number, patient identifying number, date, time, chief complaint, subordinate complaints, findings, orders, and updates to current medications list, past medication list, active problems list, and past problems list. The past encounter database maintains data about completed encounters. The fields are similar to those described for the active encounter database.

The medical content database stores fields such as lists of systems, lists of regions of the body, graphic depictions of regions of body, lists of locations of the body, graphic depictions of locations of the body, lists of problems, lists of procedures/orders, and lists of details keyed by finding type and finding location that may be selected by the use to further document findings of a particular type at a particular location.

In a first implementation, this data is organized as a tree. The root provides a starting point for navigation. Each of the children of the root is the root of a sub-tree that comprises the findings for a particular system of the body. The contents of these subtrees is any number of levels of "Place Nodes" that comprise the data associated with a region of the body (when the place is the current region displayed for navigation) or location of the body (when the place is the location selected within a region) for a particular system. Place nodes contain fields such as the identity of the place, a graphical depiction of the region, identity of the enclosing parent place, identities of sub-places that correspond to particular locations that may be selected in the place (if any), a list of problems that may be assigned to findings at the location, a list of procedures that may be ordered for the location, and the identity of corresponding places under different systems of the body.

The cryptographic key database facilitates cryptographic functions, storing both symmetric and asymmetric keys. The CPU for encrypting and decrypting network messages and for authenticating network connections uses the keys. The audit database stores transactional information pertaining to executed transactions, allowing it to be retrieved for later analysis. The order database stores pending orders for transmission to actors that will complete the orders and the results of completed orders.

Figure 23:
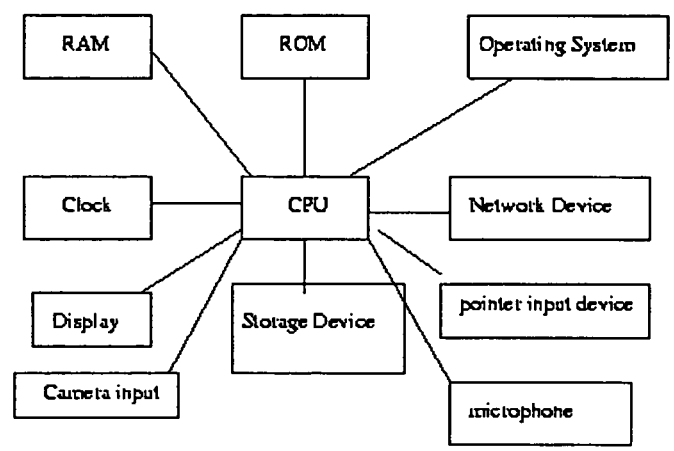
FIG. 23 is a block diagram of the client device of FIG. 21 with exemplary details.

FIG. 23 is a block diagram of the client device of FIG. 21 with exemplary details. As shown in FIG. 23, the client device includes a central processor (CPU), a RAM, a ROM, a clock, an operating system, an network interface, a display, a pointer input, a camera, a microphone, and a data storage device. In one embodiment, this functionality resides on a notebook computer such as a Sony C1 PictureBook computer with integrated camera. In another embodiment, this functionality resides on a tablet form-factor device such as the Fujitsu Stylistic 3400 (which, however, omits the camera module). The Pointer input device may be a touch screen, mouse, trackball, touch pad, or joystick. The camera may be integrated into the device as in the Sony C1 PictureBook computer, it may be a separate device capable of transferring data over a network to the client device or central controller, or it may be omitted in some embodiments. The microphone may be integrated into the device as in the Sony C1 PictureBook computer, it may be a separate device capable of transferring data over a network to the client device or central controller, or it may be omitted in some embodiments. The data storage device stores machine identity information and cryptographic information for authenticating communication. It may also act as a write buffer by storing updates to the current encounter that have not yet been transmitted to the central controller. It may also act as a cache of data read from the central controller.

There are many commercial software applications that can enable the communication required between the client device and central controller, the primary functionality being message creation and transmission. For example, the central controller may be configured as a web server, and conventional communications software such as Netscape navigator web browser from Netscape Corporation may be used by the client device to display the options and data presented by the central server to the user and to gather and transmit user input to the central controller. The user interface provided by the browser may be further augmented by interface enhancements specified in JavaScript, Java, or provided by the Java Swing user interface toolkit. For example, the X windows system provides a general method for communicating via a user interface between a client device and central controller. Alternatively, for example, the TCP/IP network protocol suite provides a method for general communication between a user interface program running on the user device and the central controller.

Because the medical information that is the focus of this invention may be of a sensitive nature and because some embodiments may use wireless communication between the user device and central controller, one embodiment encrypts data communication between different devices on a network. There are many commercial and free packages for encrypting network communication including the IPSec standard for authenticating and securing communication between two devices that communicate using the IP (Internet Protocol) standard, and including the Secure Socket Layer and HTTPs standards for securing and authenticating communication between a web browser and a web server.

While the above embodiment describes a single computer acting as a central controller, those skilled in the art will realize that the functionality can be distributed over a plurality of computers. In one embodiment, central controller is configured in a distributed architecture, wherein the databases and processors are housed in separate units or locations. Some controllers perform the primary processing functions and contain a minimum amount of RAM, ROM, and a general processor. Each of these controllers is attached to a network hub, which serves as the primary communication link with the other controllers and client devices. The network hub may have minimal processing capability itself, serving primarily as a communication router. Those skilled in the art will appreciate that an almost unlimited number of controllers may be supported. This arrangement yields a more dynamic and flexible system, less prone to catastrophic hardware failures affecting the entire system.

Handheld Device Embodiment

In a handheld device embodiment, both the central controller and client device reside on a portable computer device such as a laptop computer (e.g., Sony VAIO PCG Z505SX) or a tablet form-factor device such as the Fujitsu Stylistic 3400. In this embodiment, network communication is eliminated between the modules in favor of direct communication through local memory or storage.

Electronic Medical Record Embodiment

The invented method may be used as a part of an electronic medical record access system that provides a means of documenting medical encounters with patients. FIG. 24 is a flow chart showing how an exemplary physical exam medical system of the present invention using an exemplary method for documenting medical findings consistent with the present invention may be incorporated into an electronic medical record (EMR) system. In accordance with step 1001, the user logs into the system. The user may login via a portable computing device, or a general use device. In one embodiment, the user logs in, using a portable-computing device that is provided with an electronic medical chart GUI. In accordance with step 1002, the user may next select the task to be performed, such as entering new data, updating data, or reviewing data. In accordance with step 1003, the user then selects the patient for whom the task will be performed, which may include selecting an existing patient or opting to begin a new patient record. The user may then enter, update, review, etc., data for any of a plurality of tasks 1004, such as preliminary patient information, physical examination and assessment, diagnosis, and treatment orders. During each task 1004, the invented method described with reference to FIG. 2 may be executed to document findings, issue orders, or navigate. This allows for each task 1004 to be performed and ended directly after patient selection, without proceeding to the other tasks. It also allows for the tasks 1004 to be performed consecutively, for example, with new patients. Once a task 1004 is completed, the user may select a new patient or a new task 1004, or the user may proceed to a finishing step 1005. The finishing step 1005 allows the user to review the results of the session and to complete administrative tasks, such as submitting narratives, changing scheduling, drafting correspondence, and the like. After the finishing step 1005, the user may proceed to another patient or task, or log out of the system at step 1006.

This system provides a novel method to document both a problem type and a problem location to thereby document a finding. The key innovation is a novel method that coordinates the documentation of these factors and that coordinates "drill down" and "selection" navigation.

Another object of the invention is to document findings that comprise a problem, a location, and a state, where the state represents a modifier to the finding to represent whether the finding is positive or negative, whether a finding has been made at all, the certainty of the determination, or any combination of these factors. For example, in one embodiment, the state is chosen from the group PRESENT, NOT_PRESENT, and NO_FINDING_ENTERED. PRESENT findings represent a determination that a condition exists for a patient (e.g., "Rash on upper right thigh PRESENT".) NOT_PRESENT findings represent a determination that a condition does not exist for a patient (e.g., "Femur fracture NOT_PRESENT"). NO_FINDING_ENTERED findings represent findings for which no data have been entered. In another example, the state is chosen from the group PRESENT, SUSPECTED, NOT_PRESENT, and NO_FINDING_ENTERED, where SUSPECTED findings represent determination that a condition may be present but where certainty is lacking and where the other states are as described previously.

Another object of this invention is to document medical findings that require more detail than simply a problem, location, and state. Another object of this invention is to efficiently document multiple problems that are located near one another in the body. For example, an emergency room doctor treating a hand damaged in an industrial accident might need to document cuts to several fingers and the hand as well as broken bones in the several fingers and the hand. Such situations create a requirement for a method that efficiently coordinates navigation to different related locations, selection of related locations, and selection of multiple problems.

Another object of the invention is to provide a graphic interface that automates the clinician's process of selecting the desired convergence of diagnosis and care plan. A further object of the invention is to automate health care administrative tasks such as completion of forms, requisitions, transmittal memos, etc. to improve the accuracy of information and reduce errors in the provision of health care. Yet another object of the invention is to reduce or eliminate the need for paperwork attendant to the Physical exam and automate the creation of necessary paperwork that is required. Yet a further object of the invention is to provide an ergonomic voice, touch and/or text-accessed interface that provides enhanced efficiencies in the process and flow of medical care. Yet another object of the invention is to provide a system that allows for the seamless convergence of systems such as electronic medical records, expert software systems, and other healthcare-related and non-healthcare-related electronic data. The present invention is a method and apparatus for enhancing the Physical exam by automating and implementing medical care tasks.

According to one aspect of the present invention, a user interface, referred to as the interactive device, assists a user such a medical practitioner to automate a portion of his/her work flow, without constraining him/her to a rigid process flow and without requiring him/her to perform additional tasks, such as recording descriptive data, that would disrupt his/her work flow.

Figure 25:
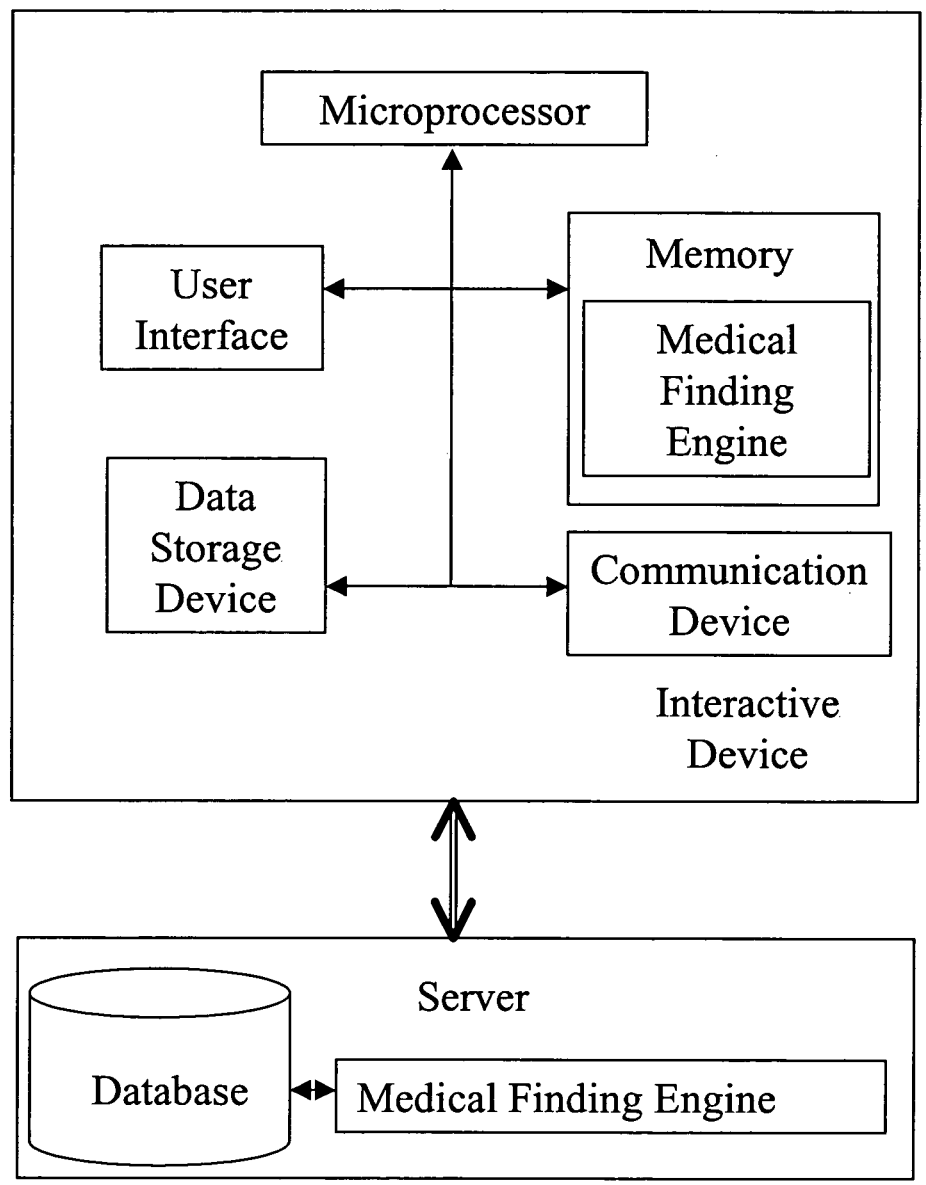
FIG. 25 is a block diagram of the functional components of an exemplary interactive device adapted to provide an interface to a physician for facilitating a physical exam session.

FIG. 25 is a block diagram of the functional components of an exemplary interactive device adapted to provide an interface to a physician for facilitating a physical exam session. Interactive device includes a microprocessor executing a computer program stored at least in part in a read only memory (ROM) and carrying out many of the steps of the present invention. Interactive device includes a communications device for communicating with a server on, which may reside additional portions of the computer program and data used in carrying out the invention. Interactive device also uses a random access memory (RAM) for temporary information storage.

Interactive device also includes at least one output interface and associated circuitry for communicating information to a user such as a physician, as well as one or more input interfaces, such as a touch sensitive screen and a microphone, with associate circuitry for receiving information from the physician. Output interface can provide information to the physician visually, audibly, or in any combination of ways. Input interfaces can allow input in any number of ways, such as by a touch screen, keyboard, voice capture, voice data recognition, voice command recognition, handwriting image capture, cognitive handwriting recognition, or any other way or combination of ways of receiving communications to the physician. Communication device or a different communication device can optionally support data ports for connection external devices, such as thermometers or blood pressure measurement devices.

The interactive device could comprise, for example, a desktop, laptop, tablet, or other type of computer. The preferred embodiment of interactive device may change as technology evolves. The components that comprise interactive device do not need to be physically incorporated into a single unit. For example, a wall display or speaker could be used as the output device. A microphone mounted in a room could be used as an input device, and additional memory may reside off the device. Any type of devices that can provide information to the physician and receive input from the physician can be used as an interactive device without departing from the scope of the invention as defined in the claims appended hereto.

Figure 26:
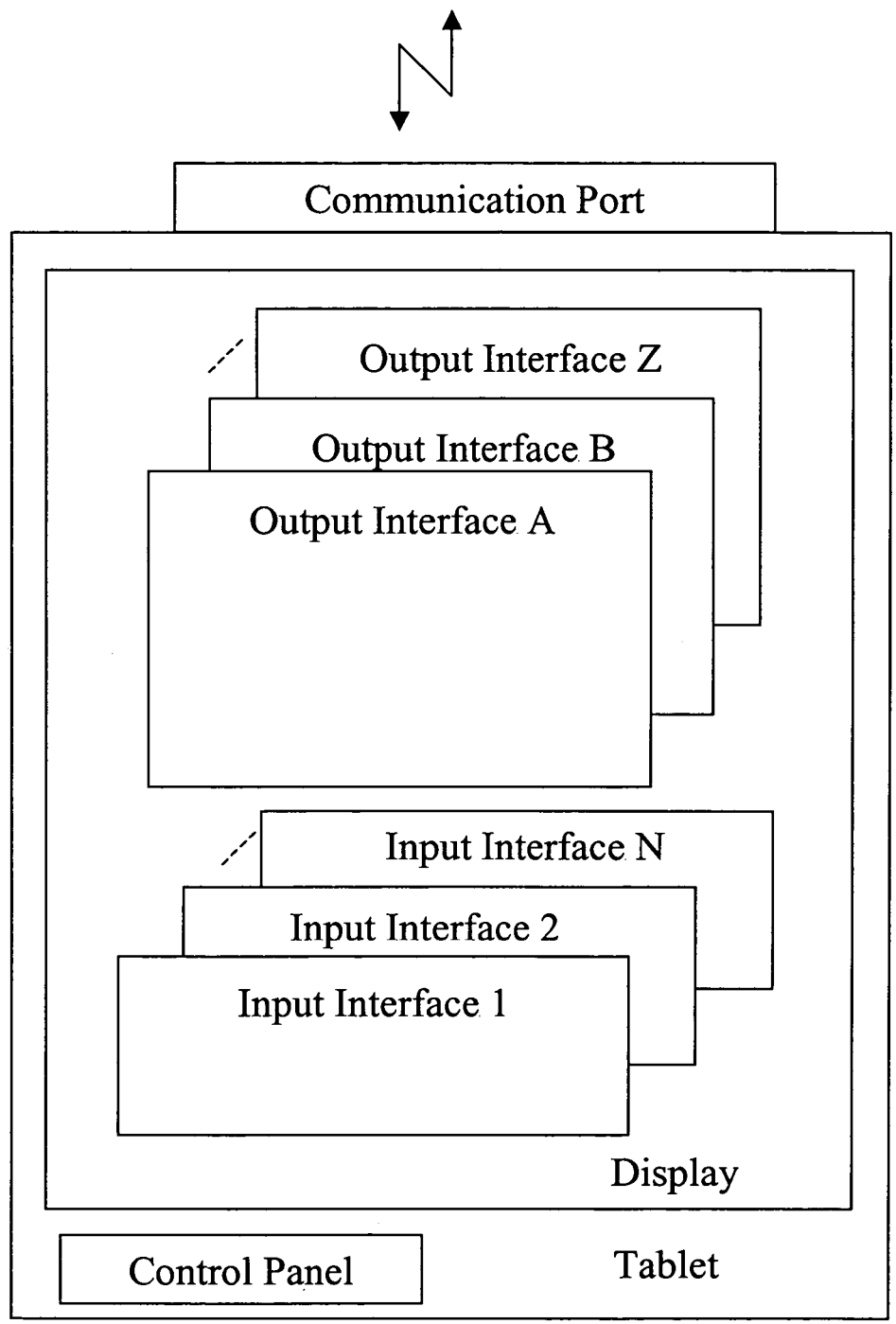
FIG. 26 shows a top view of the interactive device of FIG. 25.

FIG. 26 shows a top view of the interactive device of FIG. 25. FIG. 26 shows a preferred interactive device in the form of a handheld computing device or tablet on which a physician interface is displayed. Tablet includes a touch sensitive screen for selecting items from a displayed screen, a pen stroke area (which may be the entire screen) for entering information using pens strokes, and a microphone for accepting speech commands or data from the physician. One or more connection ports allow direct connection of one or more devices such as an electronic thermometer or blood pressure measuring device.

Figure 27:
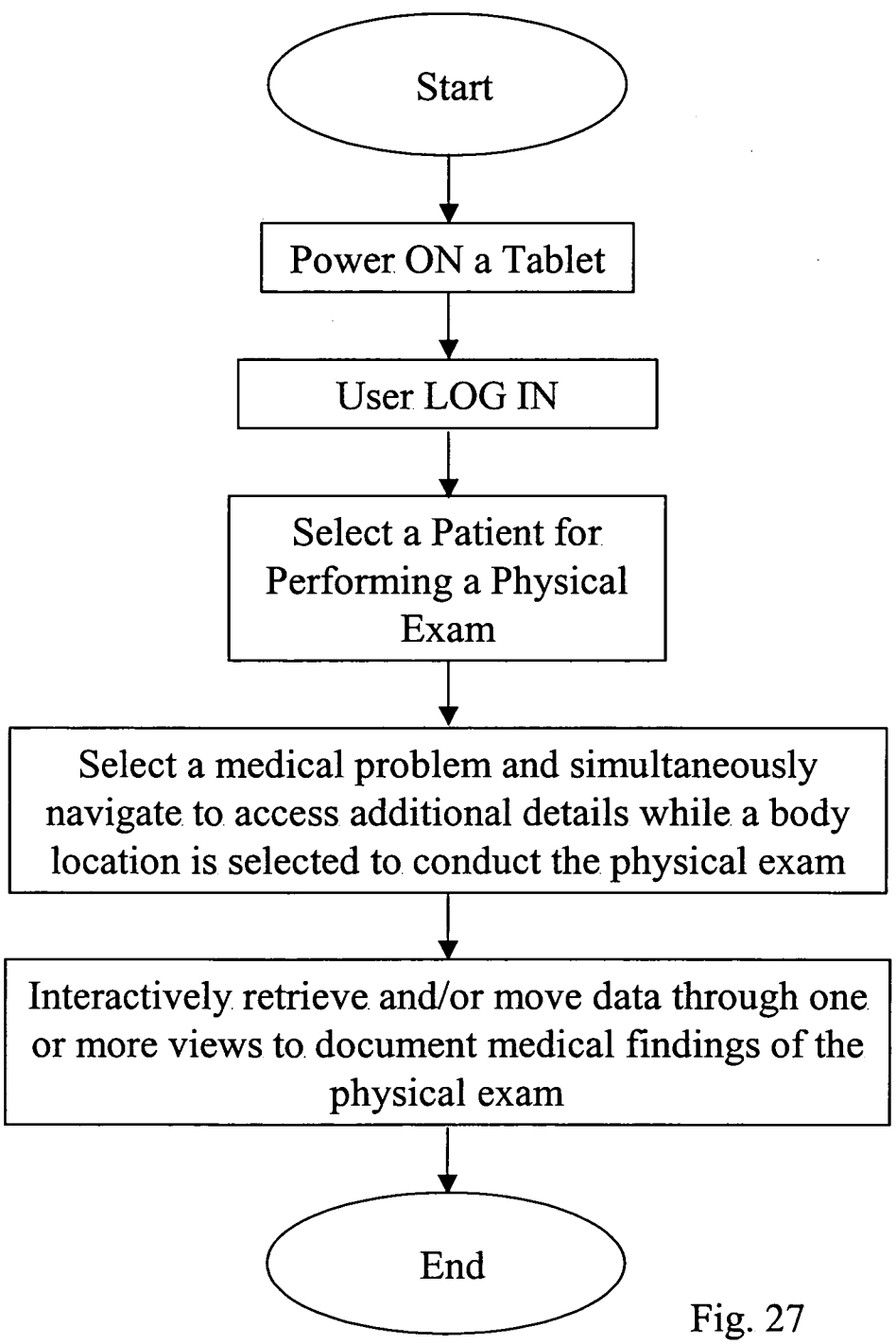
FIG. 27 is a flow chart showing the operation of the interactive device of FIG. 25.

FIG. 27 is a flow chart showing the operation of the interactive device of FIG. 25. FIG. 27 illustrates the features of a system incorporating the present invention. In a step, the user turns on the power to the tablet. Each user may be required to provide one or more passwords for software access. Certain types of information pertaining to other users or patients may require specific passwords allowing access only by appropriate individuals.

In the next step, a patient is selected by voice command or by touching the patient's name on the screen in a schedule or list as described above. Upon selection of a patient for a physical exam, a physician can enter a patient's name, select a name from the schedule, or perform a search to locate a patient. Upon selecting a patient, an interface is displayed for the selected patient in next step. A user may select a medical problem and simultaneously navigate to access additional details while a body location is selected to conduct the physical exam. The user can interactively retrieve and/or store data through one or more views to document medical findings of the physical exam.

A system for documenting one or more medical findings of a physical examination, the system includes an interactive device having an output interface and an input interface, the output interface for displaying to a user, health-related information including anatomical information having a list of body systems (optionally) and a plurality of body locations and diagnostic information having a plurality of medical problems, and the input interface for the user to navigate the displayed anatomical information and diagnostic information for deriving the one or more medical findings, each medical finding comprising at least one selected medical problem corresponding to at least one selected body location; a memory for storing a computer program; a processor for executing the computer program, the computer program processing the one or more medical findings; and a data storage device for storing the one or more medical findings.

One embodiment of the invention is based on a method for documenting medical findings of a physical examination, the method including: displaying anatomical information including a list of body systems (optionally) and a plurality of body locations, in a first view; accepting from a user a first selection from the anatomical information including at least one body system (optionally) and one or more body locations related to the physical examination; displaying diagnostic information including a plurality of medical problems, in a second view, responsive to the first selection; accepting from the user a second selection from the diagnostic information including one or more medical problems; and combining the first and second selections to derive at least one medical finding.

Another embodiment of the invention provides a system for documenting one or more medical findings of a physical examination, the system comprising: an interactive device having an output interface and an input interface, the output interface for displaying to a user, health-related information including anatomical information and diagnostic information, and the input interface for the user to navigate the displayed anatomical information and diagnostic information for deriving the one or more medical findings, each medical finding comprising at least an associated medical problem corresponding to a body location; a data storage device for storing the one or more medical findings; a memory for storing a computer program; and a processor for executing the computer program, the computer program processing the one or more medical findings, by: displaying in a first view through the output interface the anatomical information including a list of body systems (optionally) and a plurality of body locations; accepting from the user a first selection from the anatomical information including at least one body system (optionally) and one or more body locations related to the physical examination, the selected anatomical information being entered through the input interface in the first view; automatically displaying in a second view the diagnostic information including a plurality of medical problems consistent with the anatomical information, the plurality of medical problems being displayed through the output interface in a specific order selected by the user; accepting from the user a second selection from the diagnostic information including one or more medical problems, the selected diagnostic information being entered through the input interface in the second view; and combining the selected one or more body locations with the selected one or more medical problems corresponding to the one or more medical findings for the selected at least one body system (optionally).

Another alternate embodiment of the invention is based on a computer-implemented method for documenting medical findings of a physical examination, the method including: presenting to a user a list of body systems; selecting from the list of body systems at least one body system related to the physical examination; presenting to the user a first display having a plurality of body locations; selecting from the plurality of body locations at least one body location related to the physical examination; presenting to the user a second display having a plurality of medical problems; selecting from the plurality of medical problems at least one medical problem corresponding to the selected body system and the selected body location; and storing the combination of the selected body location and the selected medical problem as a medical finding for the selected body system.

Another alternate embodiment of the invention is based on a computer-implemented method for documenting medical findings of a physical examination, the method including: presenting to the user a list of body systems including a first body system related to the physical examination; selecting from the list of body systems the first body system; presenting to the user a first display of a plurality of body locations including a first body location and a second body location, wherein the first and second body locations related to the physical examination; selecting from the plurality of body locations one or more body locations including the first body location and the second body location; presenting to the user a second display having a plurality of medical problems including a first medical problem and a second medical problem; selecting from the plurality of medical problems one or more medical problems including the first medical problem corresponding to the first body location, and the second medical problem corresponding to the second body location, wherein the first and second medical problems related to the first body system; and storing a first combination of the first body location with the first medical problem, and a second combination of the second body location with the second medical problem, wherein the first and second combinations indicate a medical finding for the first body system.

Another alternate embodiment of the invention is based on a computer-implemented method for documenting medical findings of a physical examination, the method including: presenting to a user a list of body systems including a first body system, the first body system determined to be associated with the physical examination; selecting from the list of body systems the first body system; presenting to the user a first display of a plurality of body locations including a first body location, the first body location determined to be associated with the physical examination; selecting from the plurality of body locations the first body location; presenting to the user a second display having a plurality of medical problems including a first medical problem and a second medical problem, wherein the first and second medical problems determined to be associated with the physical examination; selecting from the plurality of medical problems the first and second medical problems; and storing a combination of the first body location with the first and second medical problems as a medical finding for the first body system.

Another alternate embodiment of the invention is based on a computer-implemented method for documenting medical findings of a physical examination, the method including: presenting to a user a list of body systems including a first body system, the first body system determined to be associated with the physical examination; selecting from the list of body systems the first body system; presenting to the user a first display of a plurality of body locations including a first body location and a second body location, the first and second body locations determined to be associated with the physical examination; selecting from the plurality of body locations the first and second body locations; presenting to the user a second display having a plurality of medical problems including a first medical problem, wherein the first medical problem determined to be associated with the physical examination; selecting from the plurality of medical problems the first medical problem; and storing a combination of the first and second body locations with the first medical problem as a medical finding for the first body system.

Another embodiment provides a system and method for detailing a medical finding. Such system and method may combine one or more prepared selections with on the fly created one or more selections for detailing a medical finding. On the fly created selections could have multiple input modes. For example, annotated text can be integrated with existing selection options. Another embodiment of the invention is based on an electronic media, comprising a program for performing the methods of the invention. Another embodiment of the invention is based on a computer program, comprising computer or machine readable program elements translatable for implementing the methods of the invention.

By providing an electronic tool into the hands of the physician during the patient encounter, the present invention allows real-time quality and efficiency guidance. Because the present invention assists rather than burdens the physician, he/she will use the system during the physician-patient encounter, so the diagnostic and treatment information are available electronically for automatic checking. Moreover, by providing the physician with authoritative guidelines for diagnoses and treatments, a standard level of care is provided. The physician is not constrained, however, to any diagnosis or treatment presented by the system. The physician is always free to enter the diagnosis and treatment elements that he deems appropriate.

Although the present invention and its advantages have been described in detail, it should be understood that the system and software represent the software system for healthcare professionals. For these reasons, various changes, substitutions and alterations may be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

APPENDIX A: GLOSSARY OF TERMS

The term "Current patient" refers to an individual whose identity has been selected as the subject of documentation by the user.

The term "Place of the body" is a generic way of referring to a point on or area of the body (a place may be used as either a region for navigation or a body location for selection). (see also the terms "current region of body" and "location of body").

The term "Current region of the body" is used in its broad sense. The system iteratively shows a region of the body and lets the user select actions to perform on a location in that region. One of the actions may be to change the region to be displayed. Whatever region was last chosen to be displayed is the current region of the body.

The term "Location of body" indicates a particular location or area of the body that is selected.

The term "System of the body" means a group of related structures or problems of the human body.

The term "EMR—electronic medical record" generally refers to a computer-implemented system for documenting medical findings or issuing medical orders. In an exemplary system consistent with the present invention, the EMR is typically accessed from a wireless tablet form factor device communicating with a server in a clinic.

The term "Medical finding" is used in the broad sense. This term generally covers and includes any method, design and/or device used or useful in a documented medical fact or opinion about the condition of a patient. A medical finding indicates a medical problem; some types of medical findings may also require that a body location be documented. Medical findings may simply be documented as selected or not, or they may have a state associated with them. Some medical findings may also have details associated with them.

The term "Medical problem" is used in the broad sense. This term generally covers and includes any type of medical finding e.g., "fracture", "contusion", and "pallor."

The term "Body location" is used in the broad sense. This term generally covers and includes the location of a medical finding e.g., right arm, back, and left femur.

The term "Medical finding state" generally represents a modifier to the medical finding to represent whether the medical finding is positive or negative, whether a finding has been made at all, the certainty of the determination, or any combination of these factors. For example, in one embodiment, the state is chosen from the group PRESENT, NOT_PRESENT, and NO_FINDING_ENTERED. PRESENT findings represent a determination that a condition exists for a patient (e.g., "Rash on upper right thigh PRESENT".) NOT_PRESENT findings represent a determination that a condition does not exist for a patient (e.g., "Femur fracture NOT_PRESENT"). NO_FINDING_ENTERED findings represent findings for which no data have been entered. In another example, the state is chosen from the group PRESENT, SUSPECTED, NOT_PRESENT, and NO_FINDING_ENTERED, where SUSPECTED findings represent determination that a condition may be present but where certainty is lacking and where the other states are as described previously.

The term "Annotation" generally means additional details about a medical finding. An annotation may comprise discrete elements (e.g., select the severity of a burn or laceration from a list; e.g., select another finding that details a parent finding), may comprise free-text or voice input, or may comprise graphical input.

The term "User" is used in the broad sense. The term user shall include but are not limited to medical professionals. When used without qualification, the term "user" refers to a medical professional that documents medical findings. Example users include a doctor, nurse, technician, or clinic administrative staff.

The term "System administration user" refers to a user responsible for setting up and maintaining the computer system including the generic medical content (e.g., diagrams, templates, etc.) displayed by the system.

We claim:

1. A method for documenting medical findings of a physical examination, the method comprising:
    displaying on an interface device a first interface including a first graphical representation of anatomical features;
    accepting from a user via the interface device a first selection of an anatomical feature by clicking on a specific part of the anatomical feature on the first graphical representation of anatomical features;
    displaying on the interface device a second interface including a second graphical representation of anatomical features and a first set of controls relating to a first plurality of medical conditions in response to accepting the first selection, the second graphical representation of anatomical features and the first set of controls displayed simultaneously without at least partially obstructing each other;
    accepting from the user via the interface device a second selection from the second graphical representation of anatomical features; and
    displaying on the interface device a third interface including a second set of controls relating to a second plurality of medical conditions;
    wherein the first set of controls includes a tri-state control comprising one graphical icon configured to indicate one of three states including present, not present, or not entered,
    the method further comprising:
        accepting from the user via the interface device an indication of a state of not present, the indication resulting from the user selecting the graphical icon twice and wherein the graphical icon displays a state of not entered for an empty box, a state of present for a checkmark, and a state of not present for a slash mark; and
        storing data associating the state accepted from the user with the first selection and displaying the state accepted from the user in a list of findings.

2. The method of claim 1, wherein the first graphical representation of anatomical features includes a graphical representation of a plurality of body locations.

3. The method of claim 2, wherein the first selection comprises a response indicative of one of the plurality of body locations.

4. The method of claim 1, wherein the step of displaying the first interface and the step of displaying the second interface take place in different views.

5. The method of claim 1, wherein displaying the second interface comprises displaying the second graphical representation in response to the first selection by the user, the first selection indicating a portion of anatomical features associated with the first graphical representation to be displayed, the second graphical representation including the portion of the anatomical features with greater detail.

6. The method of claim 1, wherein the second interface includes a drill down button.

7. The method of claim 1, wherein the second interface includes a change system button.

8. The method of claim 7, further comprising displaying a list of systems associated with the first selection in response to a user selection of the change system button.

9. The method of claim 1, wherein the second interface includes a procedure button.

10. The method of claim 9, further comprising displaying a list of procedures associated with the first selection in response to a user selection of the procedure button.

11. The method of claim 1, wherein the first set of controls includes an annotation control.

12. The method of claim 1, wherein the second plurality of medical conditions represents a greater level of detail than the first plurality of medical conditions.

13. The method of claim 1, wherein the second interface and the third interface include a list of recent findings.

14. The method of claim 1, wherein displaying the first interface, displaying the second interface, and displaying the third interface are performed on a wireless tablet computer including the interface device and configured for use by a physician.

15. The method of claim 1, further comprising
    accepting from the user via the interface device a third selection, the third selection including changing one control of the first set of controls; and
    combining the first selection and the third selection to derive at least one medical finding.

16. The method of claim 1, wherein the second graphical representation of anatomical features and the first set of controls are simultaneously active.

17. A device for documenting medical findings of a physical examination, the device comprising:
    an electronically readable media for storing instructions;
    a processor, associated with the electronically readable media, that executes the instructions; and
    the instructions comprising:
        instructions for displaying a first interface including a first graphical representation of anatomical features;
        instructions for accepting from a user a first selection of an anatomical feature by clicking on a specific part of the anatomical feature on the first graphical representation of anatomical features;
        instructions for displaying a second interface including a second graphical representation of anatomical features and a first set of controls relating to a first plurality of medical conditions in response to accepting the first selection, the second graphical representation of anatomical features and the first set of controls displayed simultaneously without at least partially obstructing each other, wherein the first set of controls includes a tri-state control comprising one graphical icon configured to indicate one of three states including present, not present, or not entered;

instructions for accepting from the user an indication of the state of not present, the indication resulting from the user selecting the graphical icon twice and wherein the graphical icon displays a state of not entered for an empty box, a state of present for a checkmark, and a state of not present for a slash mark;

instructions for storing data associating the state accepted from the user with the first selection;

instructions for displaying the state accepted from the user in a list of findings;

instructions for accepting from the user a second selection from the second graphical representation of anatomical features; and instructions for displaying a third interface including a second set of controls relating to a second plurality of medical conditions.

18. The device of claim 17, wherein the first graphical representation of anatomical features includes a graphical representation of a plurality of body locations.

19. The device of 18, wherein the first selection comprises a response indicative of one of the plurality of body locations.

20. The device of claim 17, wherein the instructions for displaying the first interface and the instructions for displaying the second interface effect different views.

21. The device of claim 17, wherein the instructions for displaying the second interface comprise instructions for displaying the second graphical representation in response to the first selection by the user, the first selection indicating a portion of the anatomical features associated with the first graphical representation to be displayed, the second graphical representation including the portion of the anatomical features in greater detail.

22. The device of claim 17, wherein the second graphical representation of anatomical features and the first set of controls are simultaneously active.

23. A method for documenting medical findings of a physical examination, the method comprising:

displaying on an interface device a first interface including a first graphical representation of anatomical features;

accepting from a user via the interface device a first selection of an anatomical feature by clicking on a specific part of the anatomical feature on the first graphical representation of anatomical features;

displaying on the interface device a second interface including a second graphical representation of anatomical features and a first set of controls relating to a first plurality of medical conditions in response to accepting the first selection, the second graphical representation of anatomical features and the first set of controls displayed simultaneously without obstructing each other, wherein the second graphical representation of anatomical features and the first set of controls are simultaneously active, wherein the first set of controls includes a tri-state control comprising one graphical icon configured to indicate one of three states including present, not present, or not entered;

accepting from the user via the interface device an indication of a state of not present, the indication resulting from the user selecting the graphical icon twice and wherein the graphical icon displays a state of not entered for an empty box, a state of present for a checkmark, and a state of not present for a slash mark;

combining the first selection and the state accepted from the user to derive at least one medical finding;

storing the at least one medical finding;

displaying the at least one medical finding in a list of findings;

accepting from the user via the interface device a second selection from the second graphical representation of anatomical features; and displaying on the interface device a third interface including a second set of controls relating to a second plurality of medical conditions.

* * * * *